US009226875B2

(12) United States Patent
Foshee et al.

(10) Patent No.: US 9,226,875 B2
(45) Date of Patent: Jan. 5, 2016

(54) MULTI-CONTAINER TRANSFER AND DELIVERY DEVICE

(75) Inventors: David L. Foshee, Apex, NC (US); Theodore J. Mosler, Raleigh, NC (US); Nathan R. Snell, Raleigh, NC (US)

(73) Assignee: YUKON MEDICAL, LLC, Research Triangle Park, NC (US)

( * ) Notice: Subject to any disclaimer, the term of this patent is extended or adjusted under 35 U.S.C. 154(b) by 972 days.

(21) Appl. No.: 13/375,990

(22) PCT Filed: Jun. 2, 2010

(86) PCT No.: PCT/US2010/037133
§ 371 (c)(1),
(2), (4) Date: Dec. 22, 2011

(87) PCT Pub. No.: WO2010/141632
PCT Pub. Date: Dec. 9, 2010

(65) Prior Publication Data
US 2012/0089088 A1      Apr. 12, 2012

Related U.S. Application Data

(60) Provisional application No. 61/329,431, filed on Apr. 29, 2010, provisional application No. 61/217,626, filed on Jun. 2, 2009.

(51) Int. Cl.
*B65B 39/00*      (2006.01)
*A61J 1/20*      (2006.01)
(Continued)

(52) U.S. Cl.
CPC ............. *A61J 1/2089* (2013.01); *A61J 1/1406* (2013.01); *A61J 1/1418* (2015.05); *A61J 1/201* (2015.05);
(Continued)

(58) Field of Classification Search
CPC ............ A61J 1/2089; A61J 2001/2013; A61J 2001/2017; A61J 2001/2058; A61J 2001/2065; A61J 2001/2082; A61M 5/1782
USPC ................... 141/329, 330, 100, 105, 107, 27; 604/82, 518
See application file for complete search history.

(56) References Cited

U.S. PATENT DOCUMENTS

4,576,594 A      3/1986   Greenland
4,722,733 A *   2/1988   Howson .......................... 604/411
(Continued)

FOREIGN PATENT DOCUMENTS

JP      11-0096546 A      1/1999
JP      2003-033424 A    2/2003
(Continued)

OTHER PUBLICATIONS

Korean Patent Office, PCT International Preliminary Report on Patentability and Written Opinion of the International Searching Authority for International Application No. PCT/US2010/037133 dated Feb. 22, 2011.
(Continued)

*Primary Examiner* — Jason K Niesz
(74) *Attorney, Agent, or Firm* — Christopher J. Knors; Moore & Van Allen PLLC

(57) ABSTRACT

A multi-container transfer and delivery device configured to allow multiple containers to transfer and mix their respective materials and for receiving of the mixed materials to a delivery device. The transfer device comprises a plurality of flow conduits for fluid flow between the multiple containers and the delivery device. Methods of mixing using the device and methods of sterilizing the device are described. A drug mixing kit comprising a multi-container housing with a plurality of flow conduits and a plurality of compartments for receiving containers and a transfer device is also described.

35 Claims, 18 Drawing Sheets

(51) Int. Cl.
*A61M 5/178* (2006.01)
*A61J 1/14* (2006.01)

(52) U.S. Cl.
CPC .............. *A61J 1/2017* (2015.05); *A61J 1/2058* (2015.05); *A61J 1/2075* (2015.05); *A61J 1/2096* (2013.01); *A61M 5/1782* (2013.01)

(56) References Cited

U.S. PATENT DOCUMENTS

| | | | |
|---|---|---|---|
| 5,304,165 A | | 4/1994 | Haber |
| 5,329,976 A | * | 7/1994 | Haber et al. .................. 141/25 |
| 6,364,865 B1 | | 4/2002 | Lavi et al. |
| 6,475,183 B1 | | 11/2002 | Epstein et al. |
| 6,478,771 B1 | | 11/2002 | Lavi et al. |
| 6,488,650 B1 | | 12/2002 | Epstein et al. |
| 6,575,205 B2 | | 6/2003 | Epstein et al. |
| 6,641,565 B1 | | 11/2003 | Lavi et al. |
| 6,645,181 B1 | | 11/2003 | Lavi et al. |
| 6,689,108 B2 | | 2/2004 | Lavi et al. |
| 6,689,966 B2 | | 2/2004 | Wiebe |
| 6,719,719 B2 | | 4/2004 | Carmel et al. |
| 6,723,068 B2 | * | 4/2004 | Lavi et al. .................. 604/82 |
| 6,779,566 B2 | * | 8/2004 | Engel .................. 141/25 |
| 7,081,103 B2 | | 7/2006 | Epstein et al. |
| 7,083,043 B2 | | 8/2006 | Sharon |
| 7,207,969 B2 | | 4/2007 | Epstein et al. |
| 7,523,822 B2 | | 4/2009 | Sharon |
| 7,540,863 B2 | | 6/2009 | Haindl |
| 7,862,538 B2 | * | 1/2011 | Sawhney et al. .................. 604/82 |
| 2002/0004643 A1 | * | 1/2002 | Carmel et al. .................. 604/86 |
| 2002/0007671 A1 | | 1/2002 | Lavi et al. |
| 2002/0021284 A1 | | 2/2002 | Wiebe |
| 2002/0087118 A1 | * | 7/2002 | Reynolds et al. .................. 604/82 |
| 2002/0123719 A1 | | 9/2002 | Lavi et al. |
| 2003/0023203 A1 | | 1/2003 | Lavi et al. |
| 2003/0024830 A1 | | 2/2003 | Sharon |
| 2004/0015134 A1 | | 1/2004 | Lavi et al. |
| 2004/0030285 A1 | | 2/2004 | Lavi et al. |
| 2004/0069044 A1 | | 4/2004 | Lavi et al. |
| 2006/0149189 A1 | | 7/2006 | Diamond et al. |
| 2007/0088315 A1 | | 4/2007 | Haindl |
| 2007/0156118 A1 | | 7/2007 | Ramsey et al. |
| 2009/0099547 A1 | * | 4/2009 | Radmer .................. 604/519 |
| 2010/0084041 A1 | | 4/2010 | Fehr et al. |
| 2012/0029464 A1 | | 2/2012 | Kragelund et al. |
| 2012/0330228 A1 | * | 12/2012 | Day et al. .................. 604/82 |

FOREIGN PATENT DOCUMENTS

| | | |
|---|---|---|
| JP | 2003-527933 | 9/2003 |
| JP | 2004-529739 | 9/2004 |
| JP | 2006-174988 A | 7/2006 |
| WO | 91-10417 A1 | 7/1991 |
| WO | 0172354 A2 | 10/2001 |
| WO | 02102295 A2 | 12/2002 |
| WO | WO/2007/101798 A2 | 9/2007 |
| WO | WO 2007/122209 A1 | 11/2007 |
| WO | WO 2009/026443 A1 | 2/2009 |
| WO | 2010/141632 A2 | 12/2010 |

OTHER PUBLICATIONS

Japanese Patent Office, Japanese Patent Application No. 2012-514102 Office Action dated Mar. 14, 2014, pp. 1-8.
Korean Intellectual Property Office, PCT International Search Report and Written Opinion of the International Searching Authority for International Application No. PCT/US2011/034676 dated Feb. 9, 2012.
Korean Intellectual Property Office, PCT International Preliminary Report on Patentability and Written Opinion of the International Searching Authority for International Application No. PCT/US2011/034676 date of issuance Oct. 30, 2012.
The International Bureau of WIPO, PCT International Preliminary Report on Patentability and Written Opinion of the International Searching Authority for International Application No. PCT/US2010/037133 dated Dec. 6, 2011.
European Patent Office, European Patent Application No. 11778075.9 Supplemental European Search Report dated Oct. 16, 2014, 6 pages.
European Patent Office, European Patent Application No. 10784039.9, Supplemental European Search Report dated Oct. 16, 2014, 6 pages.
USPTO; Non-Final Office Action for U.S. Appl. No. 13/695,224 dated Apr. 23, 2015, 29 pages.
USPTO; Final Office Action for U.S. Appl. No. 13/695,224 dated Aug. 27, 2015, 15 Pages.

* cited by examiner

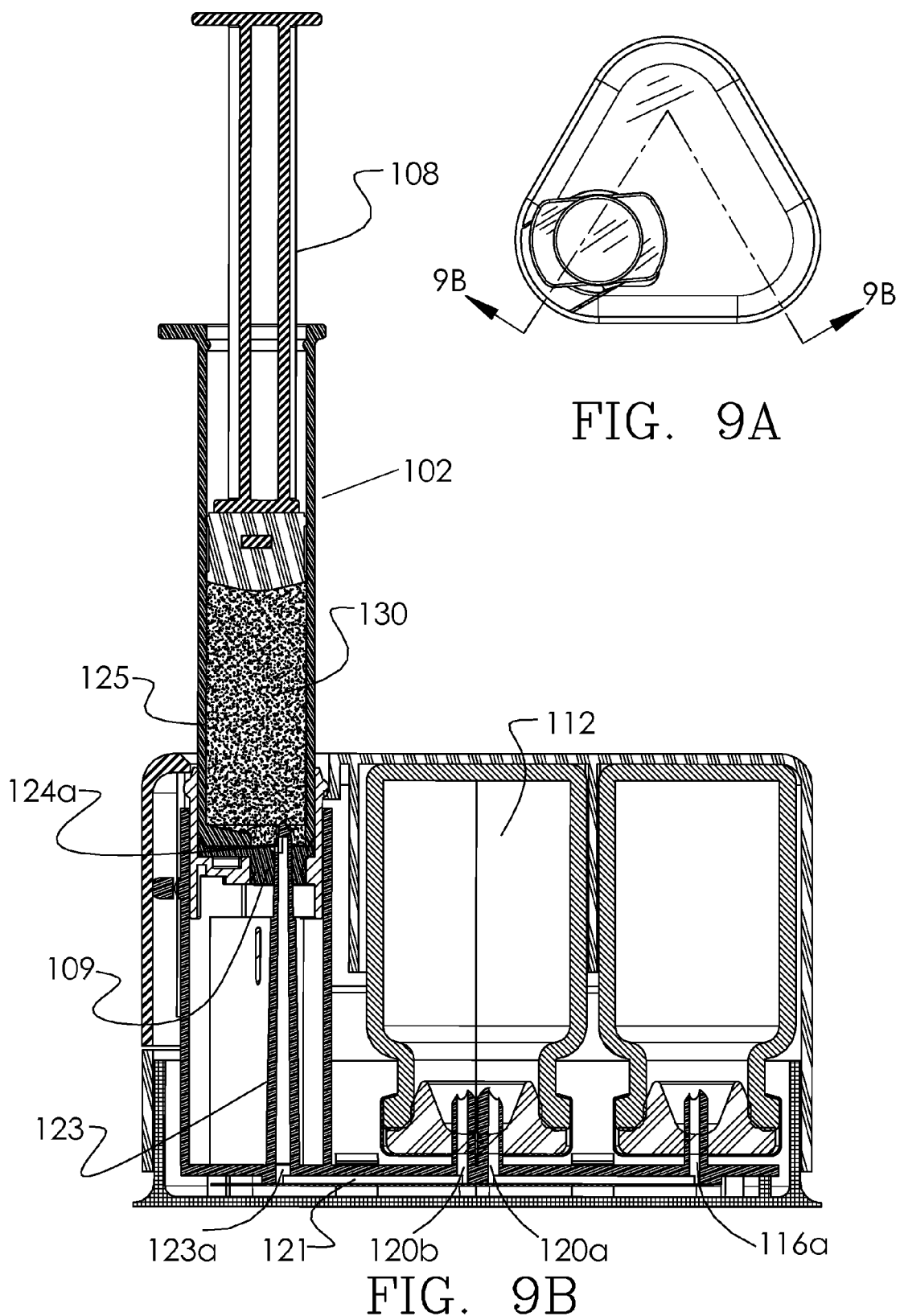

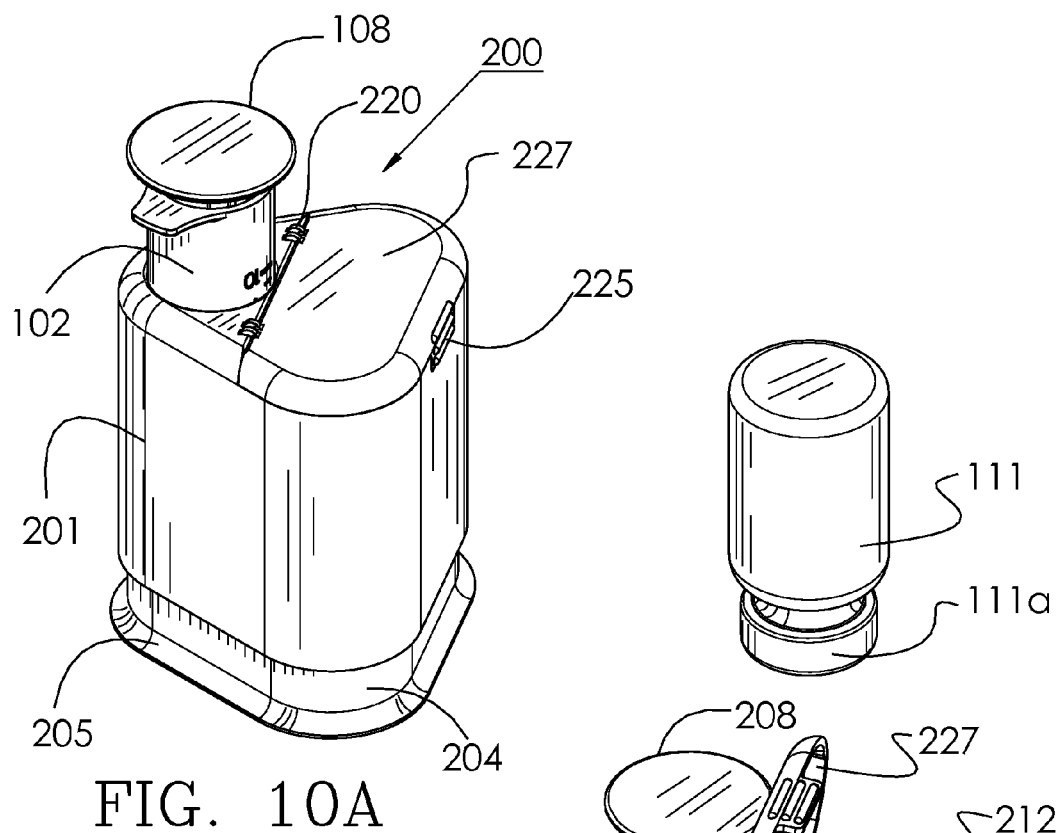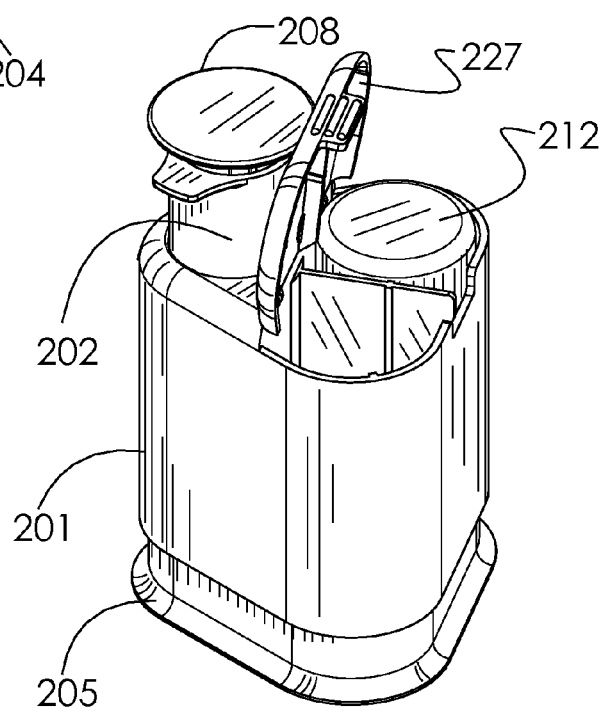
FIG. 10A
FIG. 10B

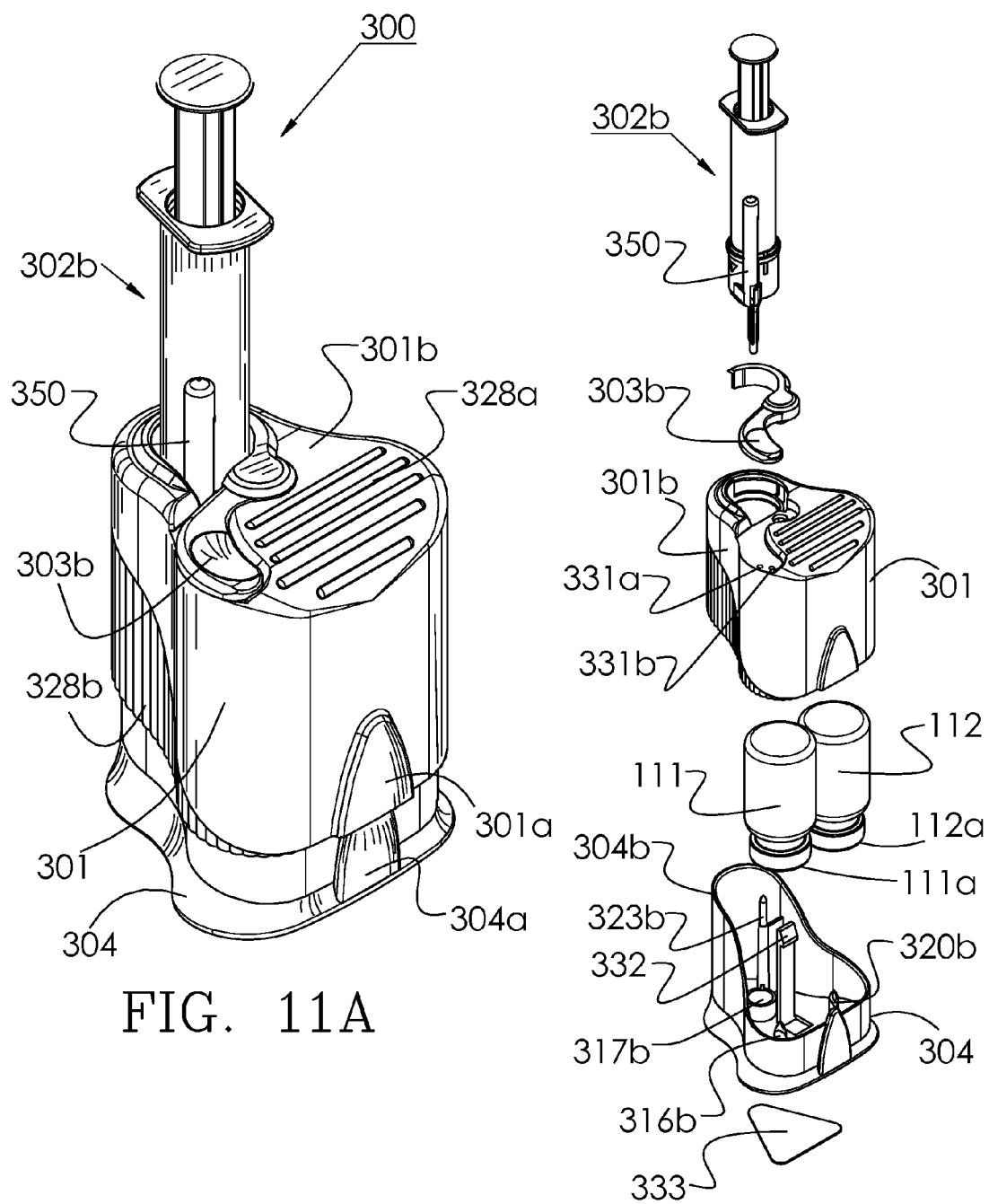

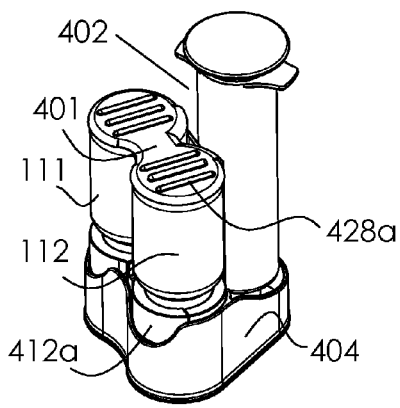
FIG. 13A
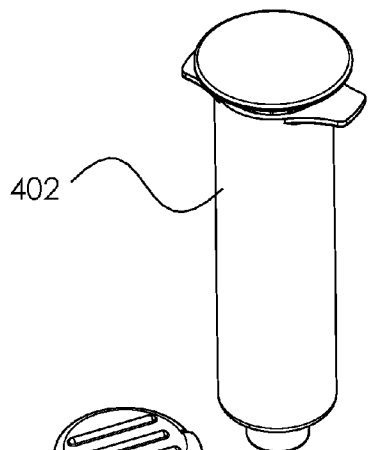
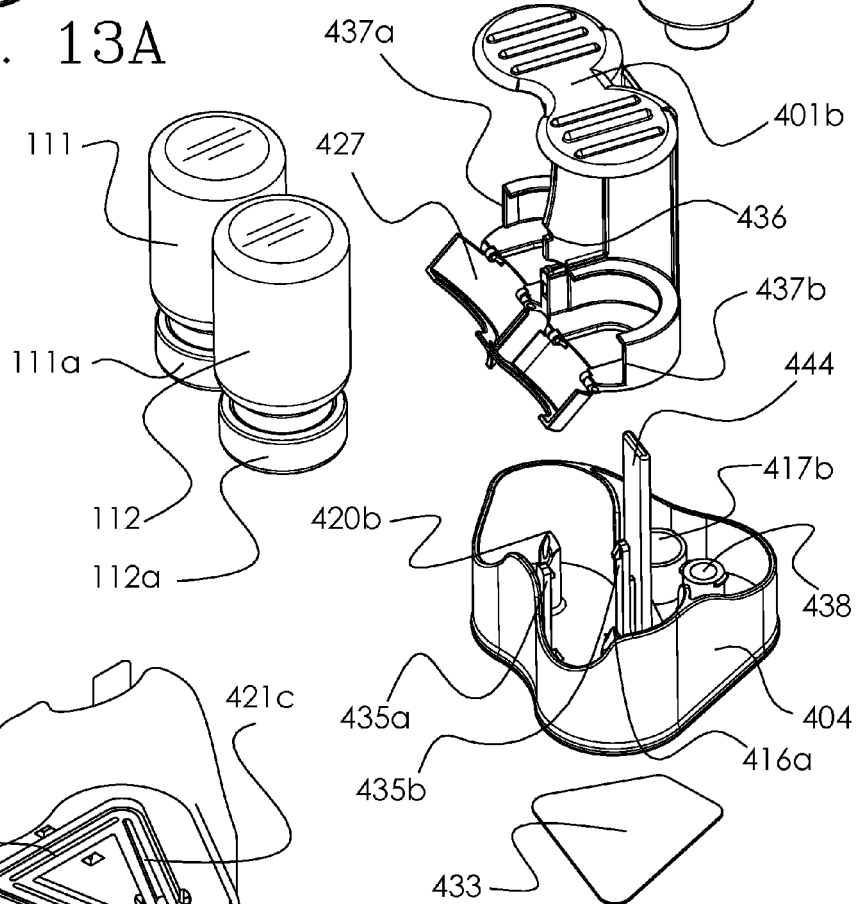
FIG. 13B
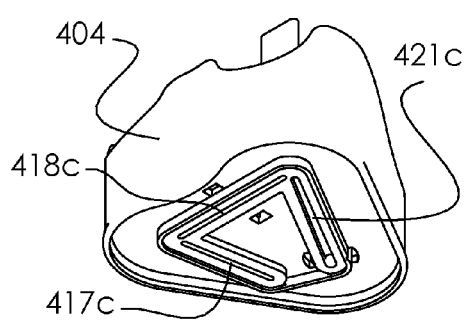
FIG. 13C

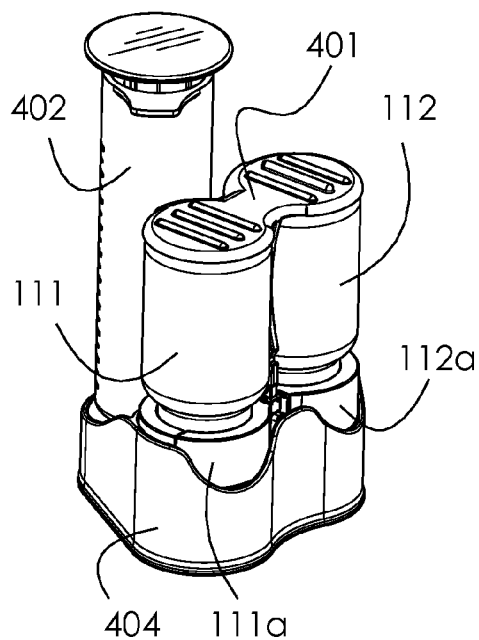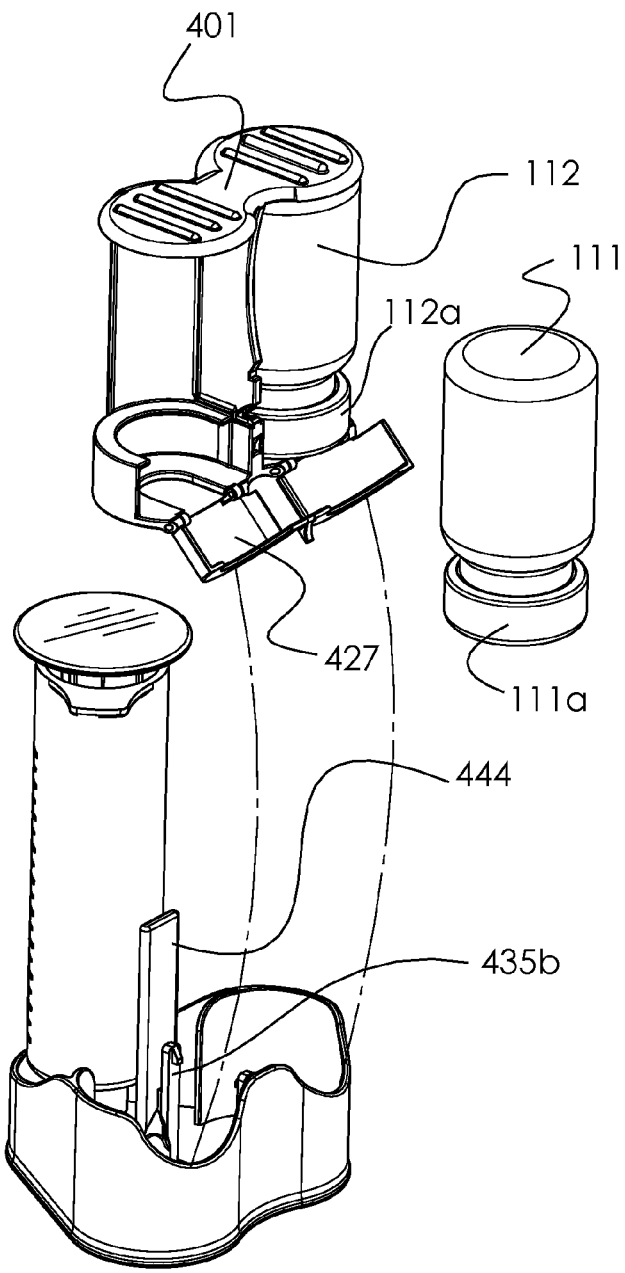
FIG. 14A
FIG. 14B

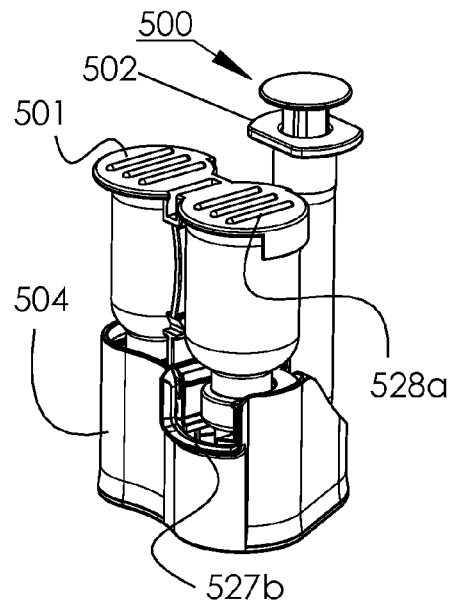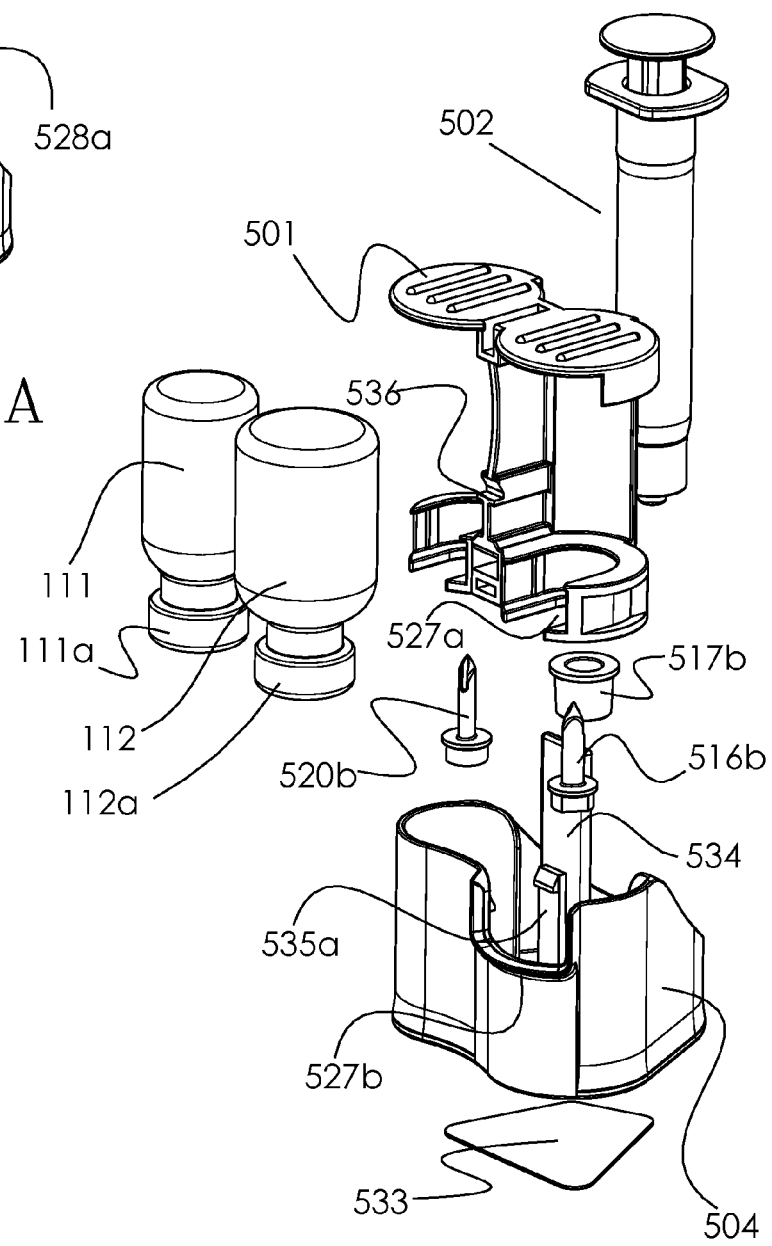
FIG. 15A
FIG. 15B

MULTI-CONTAINER TRANSFER AND DELIVERY DEVICE

CROSS-REFERENCE TO RELATED APPLICATIONS

This application is filed under the provisions of 35 U.S.C. §371 and claims the benefit of International Patent Application No. PCT/2010/037133, filed on Jun. 2, 2010 entitled "MULTI-CONTAINER TRANSFER AND DELIVERY DEVICE", which claims the benefit of priority of U.S. Provisional Patent Application No. 61/217,626, filed on Jun. 2, 2009, and U.S. Provisional Patent Application No. 61/329,431, filed on Apr. 29, 2010, all of which are hereby incorporated by reference herein in their entirety.

TECHNICAL FIELD

A multi-container transfer and delivery device configured to allow multiple containers to transfer and mix their respective materials and for receiving of the mixed materials to a delivery device. The transfer device comprises a plurality of flow conduits for fluid flow between the multiple containers and the delivery device. Methods of mixing using the device and methods of sterilizing the device are described. A drug mixing kit comprising a multi-container housing with a plurality of flow conduits and a plurality of compartments for receiving containers and a transfer device is also described.

BACKGROUND

Lyophilized and similar liquid drugs are typically provided in medicament vials with standard elastomeric closure sizes, such as 20 mm and 13 mm diameter closures. Injections of these drugs, if administered to patients intramuscularly, intravenously, subcutaneously, and the like, require syringes with needles for delivery to the patient. Needles used to administer a drug to a patient are often different from the needle or access device used to access the medicament vials. Certain needle types are special for drug vials—such as anti-coring needles—and would be inappropriate for use when injecting a patient. For instance, a pharmacy technician may use a high flow rate needle to withdraw diluent from one source, and inject it into a lyophilized drug vial. The drug is then mixed accordingly and drawn back into the syringe—or perhaps a new, sterile syringe. Oftentimes the drug preparation needle is removed, disposed of and replaced by an alternate sterile needle appropriate for the specific type of patient injection e.g. deltoid intramuscular. Because prescribed mixing and preparation of drugs vary, certain drugs need to be mixed carefully, or flow through specific sized needles; or the drug is extremely expensive so residual drug left in the vial is undesirable. This is difficult to resolve due, in part, to vial closure design and varying materials. So it may become important to pair the appropriate needle or access device with the medicament vial. Furthermore, the resultant injection process varies—the location and type of injection. Someone other than the prescriber, typically a technician or nurse, often completes the preparation and may not even be the administrator of the medication. So, there are multiple steps that can be done in error. The time of preparation can be significant, adding cost and complexity to the process. By switching needles so often and using them for drug preparation, the likelihood of needle-stick injuries increases, causing pain and concern for healthcare providers, at a minimum, and leading to potential transmission of blood borne pathogens and potentially serious diseases. The necessary aseptic preparation of a drug and its delivery is also a challenge to the caregiver and presents a safety concern for the patient if not performed well.

SUMMARY

Disclosed and described herein is a multi-container transfer and delivery device capable of addressing several of the issues described above. The disclosed device reduces the number of steps and potential errors for preparation and administration of drugs, safeguards end-users and others from accidental needle-sticks, provides for high flow conduits to expedite preparation and to protect the drug and/or blood products from mechanical/shearing forces thus preventing or eliminating drug breakdown or hemolysis. This results in drug preparation and delivery that is simplified, efficient, and effective.

In a first embodiment, a transfer device is provided. The device comprises a housing, a base, and a lower housing assembled to the base, the lower housing slidably receiving an upper housing; wherein the lower housing defines three compartments, two of the three compartments configured for receiving a container having a pierceable portion, and one of the compartments configured to secure a delivery device with a dispensing member, the delivery device having a pierceable fluid by-pass element adjacent the dispensing member. A fluidic conduit system is formed upon assembly of the base with the lower housing for providing fluid communication between at least two of the three compartments.

In a first aspect of the first embodiment, the fluidic conduit system comprises: (i) a vent; (ii) a first container accessing member having a longitudinal axis distally projecting essentially vertical from the base, and having corresponding therewith a first fluid lumen and a second fluid lumen essentially parallel with the longitudinal axis, the first fluid lumen of the first elongate container accessing member in fluid communication with the vent; (iii) a second container accessing member having a longitudinal axis distally projecting essentially vertical from the base, and having corresponding therewith a first fluid lumen and a second fluid lumen essentially parallel with the longitudinal axis, the first fluid lumen of the second elongate container accessing member in fluid communication with the second fluid lumen of the first elongate container accessing member; and (iv) an delivery device accessing member having a longitudinal axis distally projecting essentially vertical from the base, and having corresponding therewith a first fluid lumen essentially parallel with the longitudinal axis, the first fluid lumen of the third elongate delivery device accessing member in fluid communication with the second fluid lumen of the second elongate container accessing member.

In a second aspect, alone or in combination with the previous aspect of the first embodiment, the base comprises: (i) a first flow channel fluidically communicating the first fluid lumen of the first container accessing member with the vent; (ii) a second flow channel fluidically communicating the first fluid lumen of the second container accessing member with the second fluid lumen of the first container accessing member, and (iii) a third flow channel fluidically communicating the first fluid lumen of the delivery device accessing member with the second fluid lumen of the second container accessing member; the flow channels (i)-(iii) being physically isolated from each other and forming at least a portion of the fluidic conduit system upon assembly of the base and the lower housing.

In a third aspect, alone or in combination with any one of the previous aspects of the first embodiment, each of the longitudinal axes of the first container accessing member, the second container accessing member, and the delivery device accessing member distally project in the same direction relative to the base.

In a fourth aspect, alone or in combination with any one of the previous aspects of the first embodiment, the device includes the proviso that the fluidic conduit system is devoid of a flow controlling device.

In a fifth aspect, alone or in combination with any one of the previous aspects of the first embodiment, the device further comprises a first container comprising a liquid, the container operably positioned with the first container accessing member.

In a sixth aspect, alone or in combination with any one of the previous aspects of the first embodiment, the device further comprises a second container comprising a medicament, the second container operably positioned with the second container accessing member.

In a seventh aspect, alone or in combination with any one of the previous aspects of the first embodiment, the device further comprises a delivery device having the pierceable fluid by-pass element operably positioned with the delivery device accessing member.

In a second embodiment a transfer device is provided. The device comprises a housing comprising a base, and a lower housing assembled to the base, the lower housing slidably receiving a portion of an upper housing; wherein the lower housing defines multiple compartments, at least two of the multiple compartments associated with the portion of the upper housing and configured for receiving at least two containers, each having a pierceable portion associated therewith, and one of the multiple compartments configured to receive a delivery device. A fluidic conduit system is integral with the base providing fluid communication between the three compartments.

In a first aspect of the second embodiment, the fluidic conduit system comprises: (i) a vent; (ii) a first container accessing member having a longitudinal axis distally projecting essentially vertical from the base, and having corresponding therewith a first fluid lumen and a second fluid lumen essentially parallel with the longitudinal axis, the first fluid lumen of the first elongate container accessing member in fluid communication with the vent; (iii) a second container accessing member having a longitudinal axis distally projecting essentially vertical from the base, and having corresponding therewith a first fluid lumen and a second fluid lumen essentially parallel with the longitudinal axis, the first fluid lumen of the second elongate container accessing member in fluid communication with the second fluid lumen of the first elongate container accessing member; and (iv) a delivery device accessing member having a longitudinal axis distally projecting essentially vertical from the base, and having corresponding therewith a first fluid lumen essentially parallel with the longitudinal axis, the first fluid lumen of the delivery device accessing member in fluid communication with the second fluid lumen of the second elongate container accessing member.

In a second aspect, alone or in combination with the previous aspect of the second embodiment, the base comprises: (i) a first flow channel fluidically communicating the first fluid lumen of the first container accessing member with the vent; (ii) a second flow channel fluidically communicating the first fluid lumen of the second container accessing member with the second fluid lumen of the first container accessing member, and (iii) a third flow channel fluidically communicating the first fluid lumen of the delivery device accessing member with the second fluid lumen of the second container accessing member; the flow channels (i)-(iii) being physically isolated from each other and forming at least a portion of the fluidic conduit system upon assembly of the base and the lower housing.

In a third aspect, alone or in combination with any one of the previous aspects of the second embodiment, the device includes the proviso that the fluidic conduit system is devoid of a flow controlling device.

In a fourth aspect, alone or in combination with any one of the previous aspects of the second embodiment, each of the longitudinal axes of the first elongate container accessing member, the second elongate container accessing member, and the delivery device accessing member distally project in the same direction relative to the base.

In a fifth aspect, alone or in combination with any one of the previous aspects of the second embodiment, the device further comprises a first container comprising a liquid, the first container operably positioned with first elongate container accessing member.

In a sixth aspect, alone or in combination with any one of the previous aspects of the second embodiment, the device further comprises a second container comprising a medicament, the second container operably positioned with second elongate container accessing member.

In a seventh aspect, alone or in combination with any one of the previous aspects of the second embodiment, the device further comprises a syringe operably positioned with the delivery device accessing member.

In a third embodiment, method of mixing and transferring is provided. The method comprises providing a device, the device comprising: a housing comprising: a base; and a lower housing assembled to the base, the lower housing slidably receiving an upper housing; wherein the lower housing defines at least two compartments, two of the three compartments configured for receiving a container having a pierceable portion, and one of the compartments configured to engage a delivery device; and a fluidic conduit system integral with the base providing fluid communication between the at least two compartments; transferring the contents of a first container to a second container via the fluidic conduit system; and mixing at least a portion of the contents of the first container with at least a portion of the contents of the second container.

In a first aspect of the third embodiment, the fluidic conduit system comprises: (i) a vent; (ii) a first container accessing member having a longitudinal axis distally projecting essentially vertical from the base, and having corresponding therewith a first fluid lumen and a second fluid lumen essentially parallel with the longitudinal axis, the first fluid lumen of the first elongate container accessing member in fluid communication with the vent; (iii) a second container accessing member having a longitudinal axis distally projecting essentially vertical from the base, and having corresponding therewith a first fluid lumen and a second fluid lumen essentially parallel with the longitudinal axis, the first fluid lumen of the second elongate container accessing member in fluid communication with the second fluid lumen of the first elongate container accessing member; and (iv) a delivery device accessing member having a longitudinal axis distally projecting essentially vertical from the base, and having corresponding therewith a first fluid lumen essentially parallel with the longitudinal axis, the first fluid lumen of the delivery device accessing member in fluid communication with the second fluid lumen of the second elongate container accessing member.

In a second aspect, alone or in combination with the previous aspect of the third embodiment, the base comprises: (i) a first flow channel fluidically communicating the first fluid lumen of the first container accessing member with the vent;

(ii) a second flow channel fluidically communicating the first fluid lumen of the second container accessing member with the second fluid lumen of the first container accessing member, and (iii) a third flow channel fluidically communicating the first fluid lumen of the delivery device accessing member with the second fluid lumen of the second container accessing member; the flow channels (i)-(iii) being physically isolated from each other and forming at least a portion of the fluidic conduit system upon assembly of the base and the lower housing.

In a third aspect, alone or in combination with any one of the previous aspects of the third embodiment, the device includes the proviso that the fluidic conduit system is devoid of a flow controlling device.

In a fourth aspect, alone or in combination with any one of the previous aspects of the third embodiment, the device further comprises transferring at least a portion of the contents from the second container into the delivery device, the delivery device comprising a syringe.

In a fourth embodiment, a kit is provided. The kit comprises: (i) a transfer device as defined in of any one of first or second embodiments, (ii) a first container adapted for receipt by the transfer device, the first container comprising a fluid, and (iii) optionally, a packaging member.

In a first aspect of the fourth embodiment, fluid is a liquid. In other aspects, the fluid is sterilizable.

In a second aspect, alone or in combination with the previous aspect of the fourth embodiment, the packaging member comprising a first receptacle configured to receive the transfer device and the first container; and a lid sealable across the first receptacle.

In a third aspect, alone or in combination with the previous aspect of the fourth embodiment, the transfer device and the first container are operably assembled for use.

In a fourth aspect, alone or in combination with the previous aspect of the fourth embodiment, the kit further comprises a second container.

In a fifth aspect, alone or in combination with the previous aspect of the fourth embodiment, the packaging member is configured to separately receive second container in a second receptacle.

In a sixth aspect, alone or in combination with the previous aspect of the fourth embodiment, the transfer device and the second container are operably assembled for use.

In a fifth embodiment, a method of packaging a transfer device for sterilization is provided. The method comprises providing a packaging member, the packaging member comprising: a first receptacle configured to receive a transfer device optionally with a first container; and optionally, a second receptacle configured to separately receive a second container comprising a material sensitive to a sterilization condition; receiving a transfer device into the first receptacle, the transfer device comprising a housing comprising: a base; a lower housing assembled to the base, the lower housing slidably receiving a portion of an upper housing; wherein the lower housing defines multiple compartments, at least two of the multiple compartments associated with the portion of the upper housing and configured for receiving at least two containers, each having a pierceable portion associated therewith, and one of the multiple compartments configured to receive a delivery device; and a fluidic conduit system integral with the base providing fluid communication between the three compartments; and sealing the first receptacle.

In a first aspect of the fifth embodiment, the method further comprises receiving the second container into the second receptacle.

In a second aspect, alone or in combination with the previous aspect of the fifth embodiment, the method further comprises receiving the second container into the second receptacle after completion of a sterilization condition.

In a third aspect, alone or in combination with the previous aspect of the fifth embodiment, the method further comprises sealing the second receptacle.

In a fourth aspect, alone or in combination with the previous aspect of the fifth embodiment, sealing the first receptacle and the second receptacle.

In a fifth aspect, alone or in combination with the previous aspect of the fifth embodiment, the method further comprises a lid is separably removable from the first receptacle and the second receptacle.

In a sixth aspect, alone or in combination with the previous aspect of the fifth embodiment, the sterilization condition is thermal, high energy radiation, or chemical.

In a seventh aspect, alone or in combination with the previous aspect of the fifth embodiment, the second container comprises a biologic drug.

In a sixth embodiment, a method of sterilization is provided. The method comprises packaging a transfer device optionally with a first container in a packaging member, the packaging member comprising: a first receptacle configured to separately receive the transfer device and the optional first container; and a second receptacle configured to separately receive a second container; sealing the first receptacle sterilizing the transfer device and the optional first container with a sterilization condition; introducing a second container to the second receptacle, the second container comprising a material sensitive to the first sterilization condition; and optionally sealing the second receptacle.

In a first aspect of the sixth embodiment, the second container comprises a biologic drug.

In a second aspect, alone or in combination with the previous aspect of the sixth embodiment, the sterilization condition is thermal, high energy radiation, or chemical.

In a third aspect, alone or in combination with any one of the previous aspects of the sixth embodiment, the first container and/or the second container is introduced to the respective first receptacle and second receptacle in an aseptic environment

BRIEF DESCRIPTION OF THE DRAWINGS

FIGS. 9A-9B are section plane and corresponding cross-sectional views of the transfer and delivery device of FIG. 1 in an activated state.

FIGS. 10A-10B are perspective views of a second embodiment of a transfer and delivery device, as disclosed and described herein.

FIGS. 11A-11B are a perspective view and exploded view of a third embodiment of the device, as disclosed and described herein.

FIGS. 13A-13C are perspective views and an exploded view of the fourth embodiment of the device as disclosed and described herein.

FIGS. 14A-14B are perspective views of an aspect of the fourth embodiment of the transfer and delivery device as disclosed and described herein.

FIGS. 15A-15B are a perspective view and exploded view of a fourth embodiment of the transfer and delivery device as disclosed and described herein.

DETAILED DESCRIPTION

Figure 1:
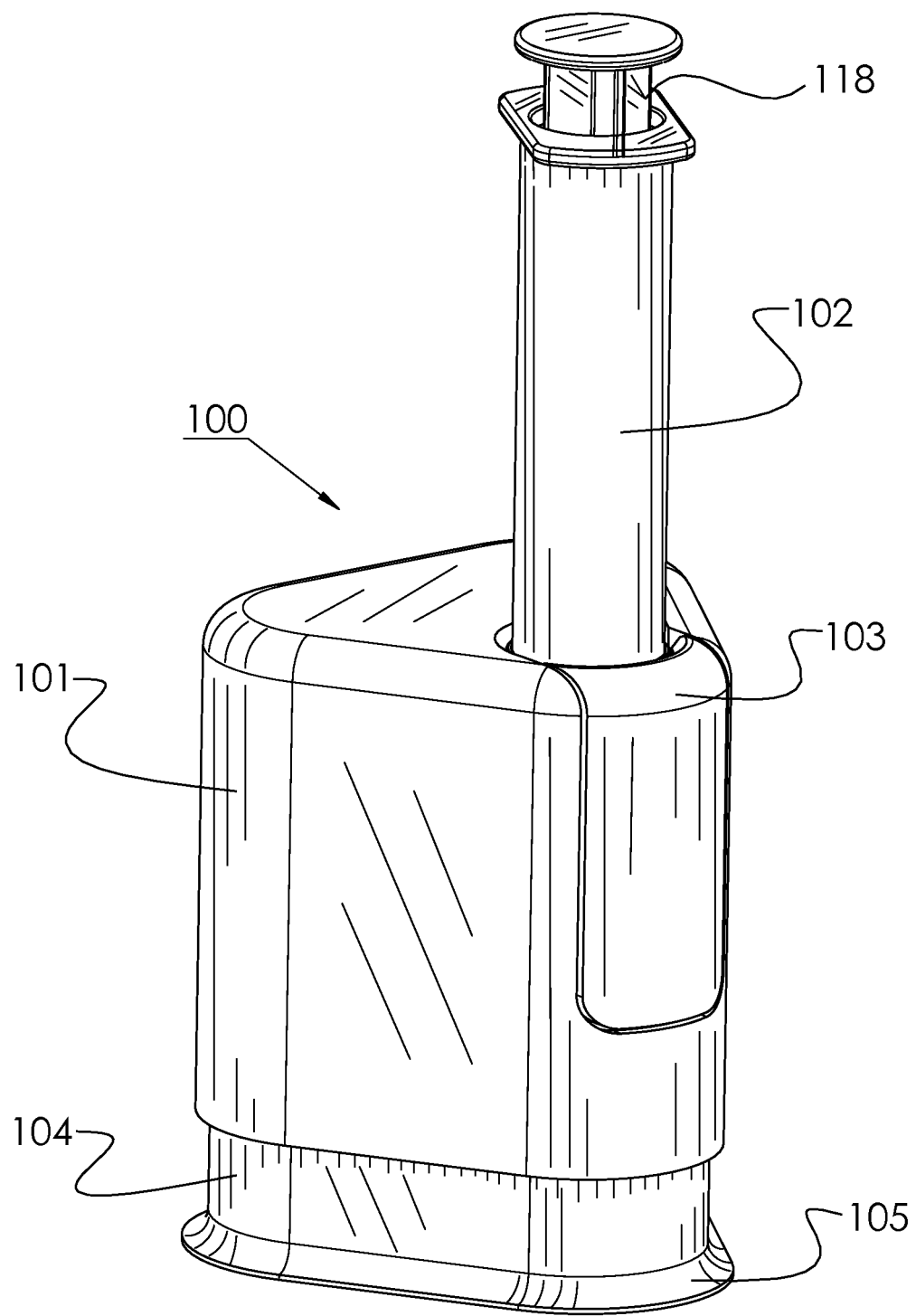
FIG. 1 is a perspective view of a transfer and delivery device as disclosed and described herein.

Throughout the specification, the term "fluid" as used herein is inclusive of gaseous, liquid, and combinations of gas and liquid medium unless specifically designated as limited to a particular medium.

Throughout the specification, the term "media" as used herein is inclusive of fluids and solid form mediums unless specifically designated as limited to a particular medium. In one aspect the media is diluent or liquid. In another aspect, the media is a medicament, which can be a pharmaceutical or biologic agent. The form of the medicament is not limited, and can be, for example, a solid, powder, liquid, dispersion, suspension, emulsion, gel, or combination thereof.

Throughout the specification, the phrases "first container" and "first media container" are used interchangeably. This container is also referred to as a "vial" unless otherwise stated, without any express or implied limitation to the scope of any claim, and are inclusive of any device with similar functionality to that of a vial, but not necessarily the structure of a vial.

Throughout the specification, the phrases "second container" and "intermediate media container" are used interchangeably. This container is also referred to as a "vial" unless otherwise stated, without any express or implied limitation to the scope of any claim, and are inclusive of any device with similar functionality to that of a vial, but not necessarily the structure of a vial.

Throughout the specification, the term "liquid" as used herein is inclusive of suspensions, oil-in-water emulsions, water-in-oil emulsions, and liquids with or without dissolved, dispersed, or contained solids irrespective of the size of the solids or the amount present.

Throughout the specification, the phrases "dual vial access device," "drug reconstitution device," "transfer and delivery device" and "fluid transfer and delivery device" are used interchangeably, unless otherwise stated, without any express or implied limitation to the scope of any claim. As is understood by one having ordinary skill in the art, a fluid transfer and delivery device provides for introduction of fluid from one container to another, while a fluid control device may include flow control means for diverting, metering, or interrupting flow between at least two flow paths.

Throughout the specification, the phrases "fluid delivery container", "final media container" "delivery device", and the term "syringe" are used interchangeably unless otherwise stated, without any express or implied limitation to the scope of any claim, and are inclusive of any device with similar functionality to that of a syringe, but not necessarily the structure of a syringe.

Throughout the specification, the phrase "biologic drug" is inclusive of any substance that is made from a living organism or its products and is used in the prevention, diagnosis, or treatment of diseases. Biologic drugs include, without limitation, antibodies, interleukins, antibiotics, and vaccines. The phrase "biologic drug" is also known as, and is herein inclusive of "biologics", "biologic agent" and "biological agent."

The fluid transfer and delivery device for the transfer of fluids between containers herein disclosed and described can be configured in a variety of ways. The device may be used in connection with the transfer of a fluid into a container in which there is a vacuum. Any piercing members are designed to penetrate elastomeric septums, sealing the containers.

In one aspect, a multi-container transfer and deliver device is configured to allow multiple containers to transfer and mix their respective materials, and for receiving of the mixed materials to a fluid delivery device. The transfer system comprises a plurality of flow conduits for fluid flow between the multiple containers and the fluid delivery device. A drug mixing kit comprising a multi-container housing with a plurality of flow conduits, a plurality of compartments for receiving containers, and a fluid delivery device is described.

The multi-container transfer and delivery device disclosed and described herein can be operated easily and safely by the user, so that drug preparation and administration may be achieved by the user in a reduced number of steps. It can be inexpensively produced and assembled. The system is suitable for dissolving a medicament as with a reconstitution process, and also for mixing fluids, for transferring a gas, etc.

In one aspect, a multi-container transfer and delivery device is provided wherein the device comprises a collapsible housing which may include a first, an intermediate, and a final portion, each portion comprising at least one media container having respective media container accessing means (e.g., spike, blunted cannula, luer fitting, or the like, with one or more lumens) for sealably accessing the media containers via an external force. The containers may be integral with the device and may be sealably accessed by, but is not limited to, spike or cannula penetration, displacement of a deformable member for example, a needle-free valve, displacement of a rigid or semi-rigid member such as a luer fitting, or any combination of these or their like. One or more of the media containers may already be sealably accessed upon its manufactured device assembly e.g. a syringe connected via a luer fitting, prior to the user providing the external access force.

The term "collapsible", as it pertains to the housing, may refer to being slidably received by the housing, deformable, telescoping, or any combination thereof. The transfer and delivery device media containers may include standard drug vials for the first and intermediate media containers, and a syringe for the final media container.

A first media container accessing means may comprise at least one first fluid lumen and optionally one vent lumen open proximal to its distal end; the vent lumen may terminate in a filtering means, such as hydrophobic vent media. While it may be intuitive to include flow control devices, such as a check valve, it is been surprisingly found that the addition of such a flow control device diminishes or eliminates the ability to recover from a mistake or may lead to over-pressurization of the system. Thus, in at least one aspect, the fluidic system is devoid of any flow controlling devices, such as check valves, as well as two-position valves, which can cause confusion as to which compartments are connected.

An intermediate media container accessing means may comprise at least one intermediate fluid lumen and a second intermediate fluid lumen, each open proximal to its distal end. The at least one intermediate fluid lumen may be in communication with at least one first fluid lumen. The final may include a fluid delivery container, accessible by a final portion fluid delivery container accessing means. A final fluid delivery container accessing means may include a final fluid lumen open proximal to its distal end and may be in fluid communication with the second intermediate fluid lumen. The fluid delivery container may be reversibly connectable to the housing and may be, but is not limited to, a syringe. The fluid delivery container may be accessed through an integrated, penetrable septum or may be sealably connected by way of a standard male/female Luer arrangement which may be of the luer lock or Luer slip. The housing may employ a locking mechanism for reversibly securing the fluid delivery container.

The multi-container transfer and delivery device can comprise varying container access member lengths, or may include varied gaps between container septums and access members, or similar means in the pre-access state in order to allow for sequencing of the first, intermediate, and final accesses upon application of an external force.

The multi-container transfer and delivery device in combination with any of the preceding aspects above can comprise a syringe with a needle safety mechanism.

The multi-container transfer and delivery device in combination with any of the preceding aspects above can comprise a flange at its base to allow for stable use on a generally flat, horizontal surface In a fourth aspect of the enclosed embodiment, the multi-container transfer and delivery device in combination with any of the preceding aspects above may comprise one or more slip-resistant members, e.g. foam pads or rubber bumpers, at its base.

The multi-container transfer and delivery device in combination with any of the preceding aspects above can utilize coatings and or lubrication e.g. silicone oil to reduce the external force required to activate the device and/or to reduce penetration forces of the accessing members and containers.

The multi-container transfer and delivery device in combination with any of the preceding aspects above can provide at least one mixing element in series with any of the first, intermediate or final conduits. The mixing element may be but not is limited to a static mixer.

The multi-container transfer and delivery device in combination with any of the preceding aspects above can be configured with an opening or access door such that a media container may be inserted by the user after manufacturing assembly.

Thus, referring now to FIG. 1, a perspective view of transfer and delivery device 100 comprising upper housing 101 configured to accept syringe 102, which is secured by a locking means 103 and lower housing 104, is shown. Flange 105 is positioned about the base of the lower housing. Likewise, a flange may also be positioned about the upper housing.

Figure 2:
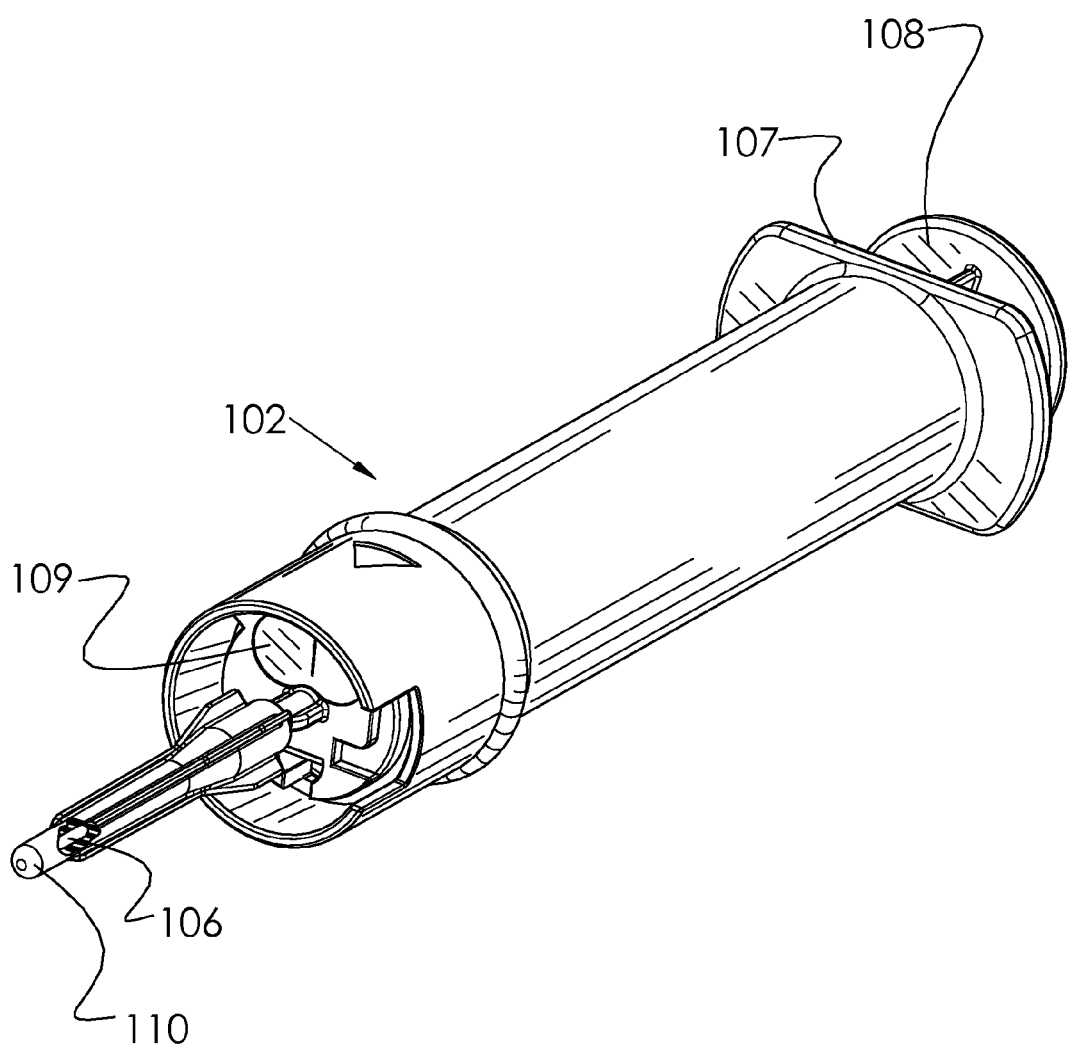
FIG. 2 is a perspective view of a detached delivery device as disclosed and described herein.

FIG. 2 is a perspective view of detached syringe 102 comprising a first end terminating in needle 106, second open end 107 for accepting a slidable plunger rod 108 for controlling interior volume and pressure, and penetrable septum 109 positioned adjacent the needle, for allowing fluid communication e.g., fluid by-pass element (e.g., syringe septum) with the interior volume of syringe. The first end needle is adapted to accept a removable, sealing needle cover 110 or, optionally, a needle safety mechanism not shown. Alignment features (not shown) can be used to allow syringe to assemble in a predetermined manner with upper housing 101.

Figure 3A:
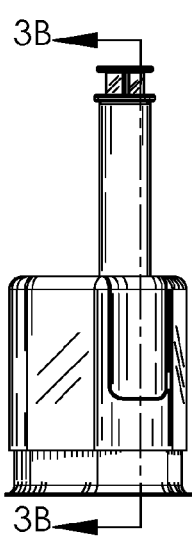
FIGS. 3A-3B are section plane and corresponding cross-sectional views of the transfer and delivery device of FIG. 1 in an initial state, as disclosed and described herein.
Figure 3B:
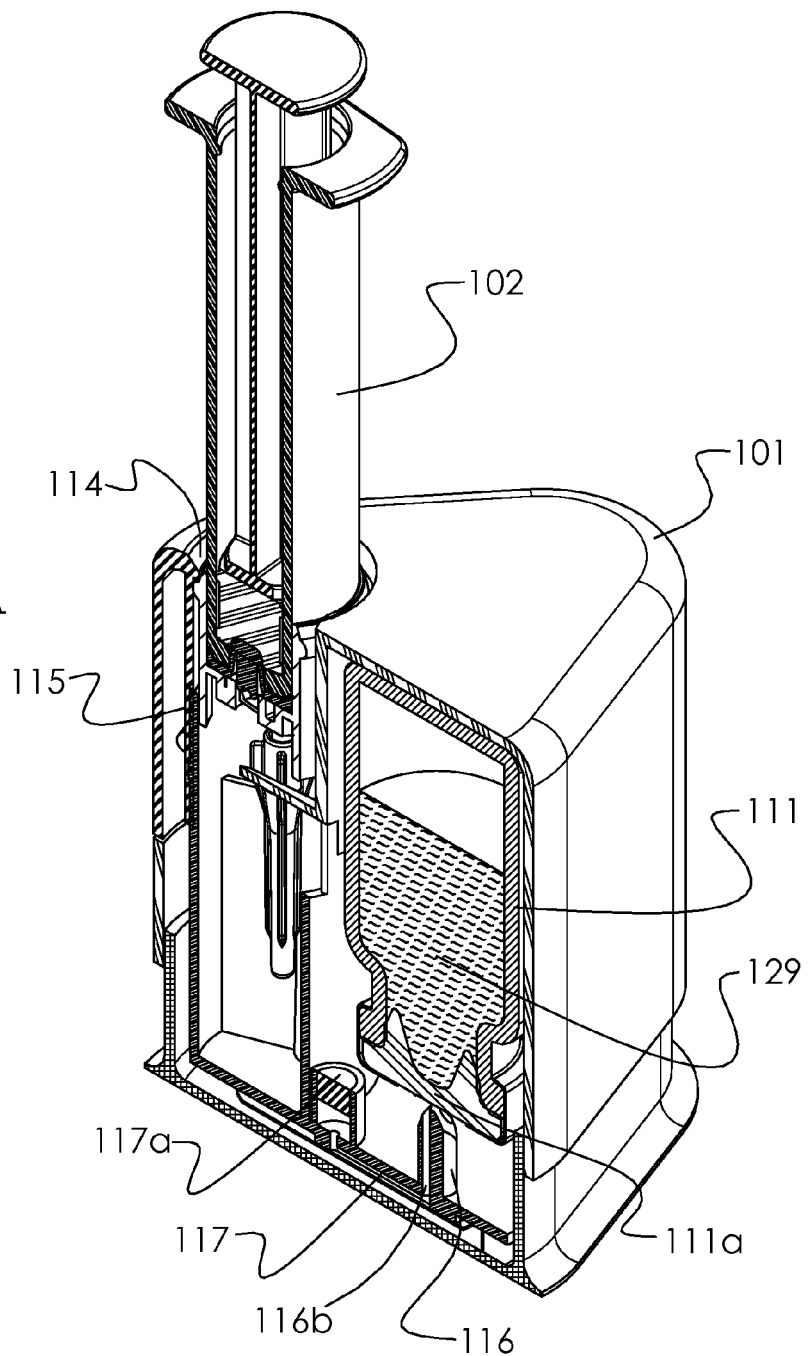
Figures 4A, 4B:
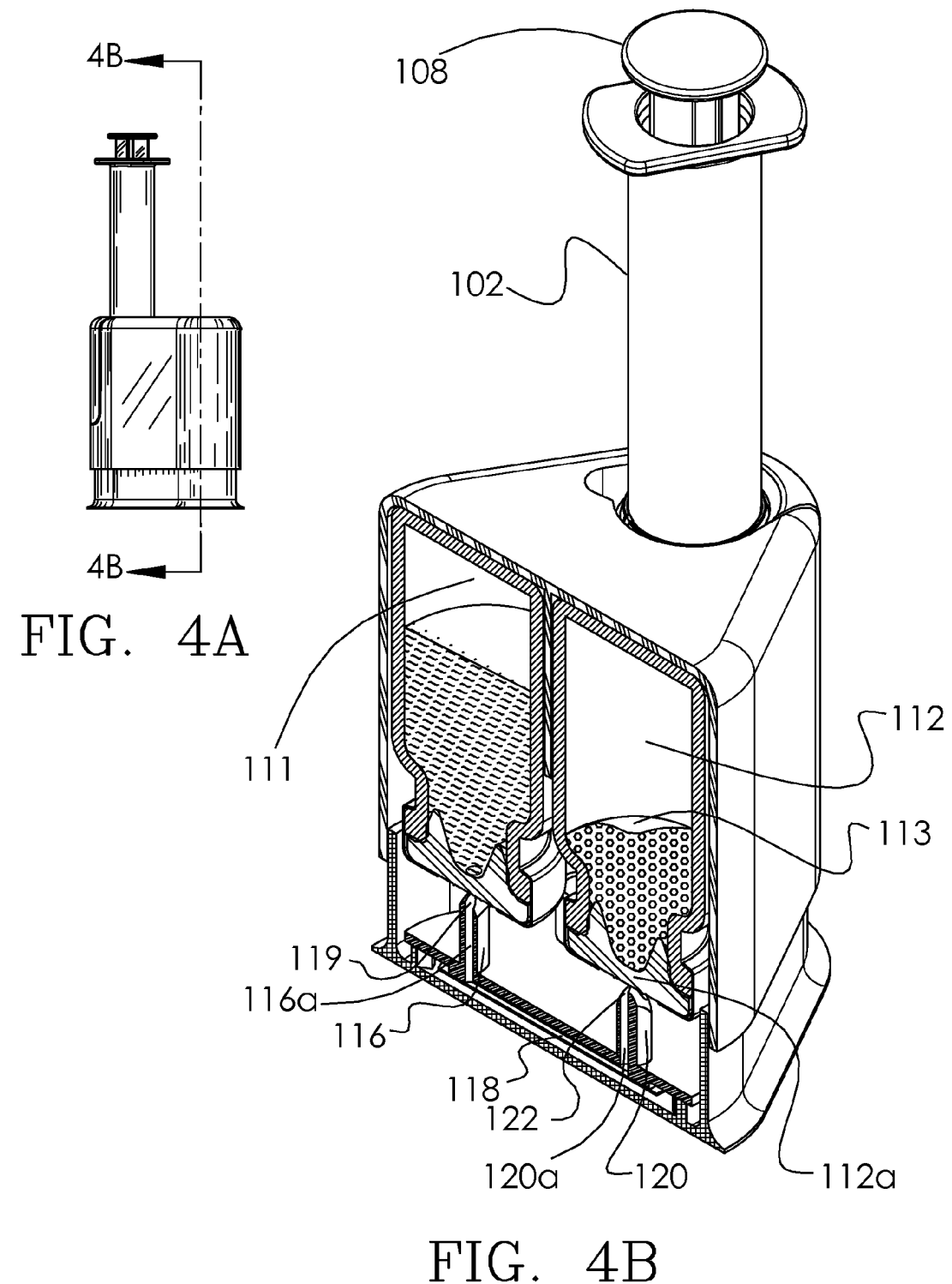
FIGS. 4A-4B are section plane and corresponding cross-sectional views of the transfer and delivery device of FIG. 1 in an initial state, as disclosed and described herein.
Figure 5A:
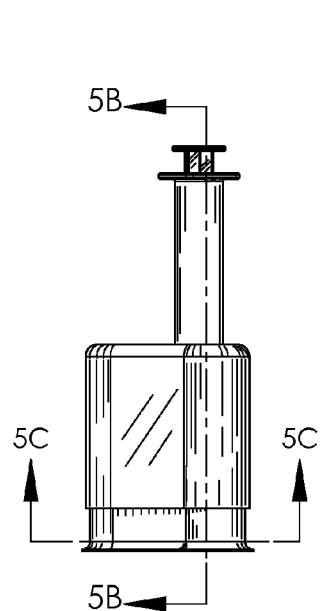
FIGS. 5A-5C are section plane and corresponding cross-sectional views of the transfer and delivery device of FIG. 1 in an initial state, as disclosed and described herein.
Figure 5B:
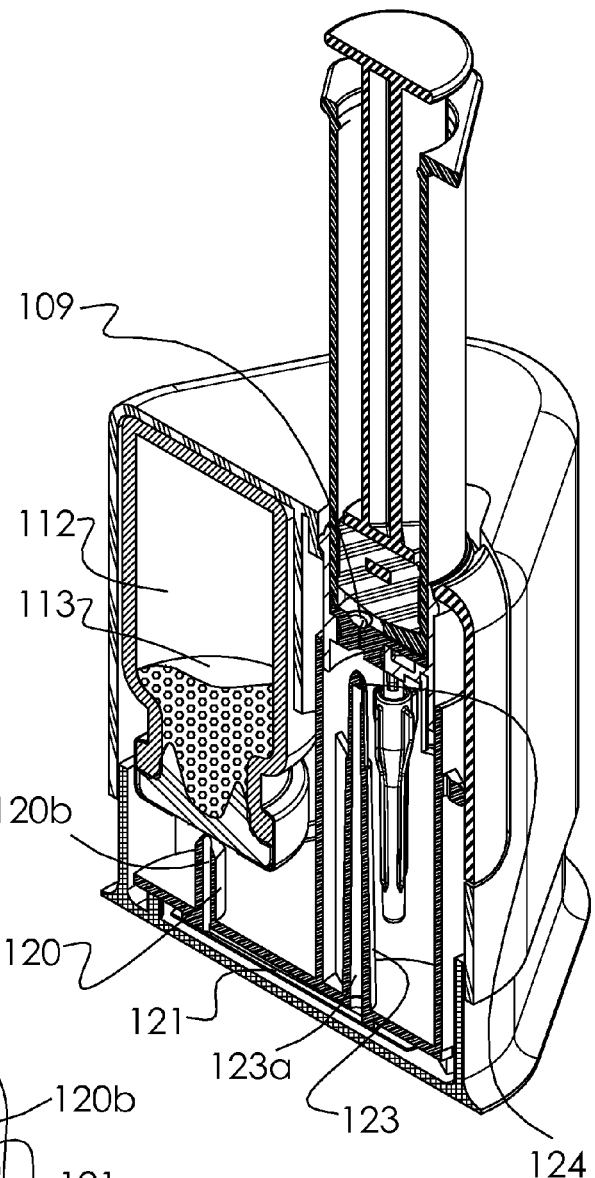
Figure 5C:
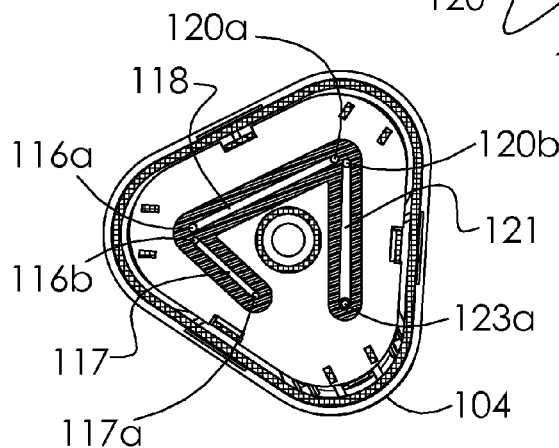

FIGS. 3A-5C are section plane and corresponding cross-sectional views of the first embodiment in an initial state, detailing the flow conduits, spikes, and vent. Referring now to FIGS. 3A & 3B, first container 111 having penetrable septum 111a contains fluid 129. The syringe of FIG. 2 is reversibly connected to the upper housing by locking feature 114 and loaded by cantilever spring 115, the locking feature integrated with or attached to the housing. First container accessing member 116 (also referred to as spike 116) terminates in a first point and comprises a first fluid lumen 116a and a vent lumen 116b, each open proximal to its distal end 119 (visible in FIG. 4B). Vent conduit 117 connects vent lumen 116b of spike 116 with vent 117a. Referring to FIGS. 4A & 4B, intermediate container 112, having a penetrable septum 112a, contains media 113, for example a reconstitutable or concentrated drug. Intermediate container accessing means 120 (also referred to as spike 120) terminates in a second point and comprises a first intermediate fluid lumen 120a and a second intermediate fluid lumen 120b, each open proximal to distal end 122. First fluid conduit 118 connects first fluid lumen 116a with first intermediate fluid lumen 120a. Referring now to FIGS. 5A & 5BA, final container accessing means 123 (also referred to as spike 123) terminates in a point or blunted cannula, and comprises fluid lumen 123a open proximal to its distal end 124. Second fluid conduit 121 connects second intermediate lumen 120b with final fluid lumen 123a.

Conduits 117, 118 and 121 are physically isolated from each other. The dual lumens of the spikes connect these isolated fluid conduits together to provide at least a portion of a fluidic conduit system. In one aspect, a fluidic conduit system is formed upon assembly of a base with the lower housing and provides fluid communication between at least two of the spikes or a spike and the vent of the device. Thus, vent lumen 116b of spike 116, vent conduit 117, and vent 117a are in fluidic communication. Fluid lumen 120a of spike 120, first fluid conduit 118, and fluid lumen 116a of spike 116 are in fluidic communication. Fluid lumen 123a of accessing means 123, second fluid conduit 121, and fluid lumen 120b of spike 120 are in fluidic communication.

FIGS. 6A-6D are section plane and corresponding cross-sectional views of the first embodiment device in its activated state. Access members have sealably pierced their respective media containers. Fluid communication is made between the vent conduit 117, first container 111, first fluid conduit 118, intermediate container 112, second fluid conduit 121 and interior volume 125 of syringe 102. First container contains fluid 129, as shown, just prior to its fluid being pulled into the intermediate container.

Figure 6A:
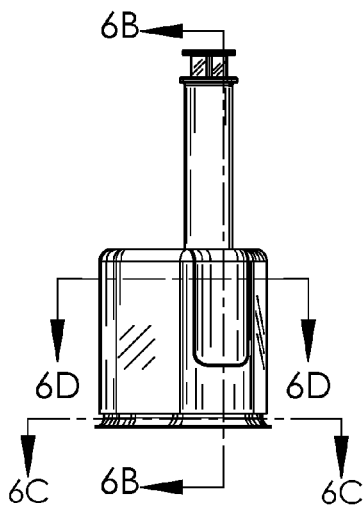
FIGS. 6A-6D are section plane and corresponding cross-sectional views of the transfer and delivery device of FIG. 1 in an activated state, as disclosed and described herein.
Figure 6C:
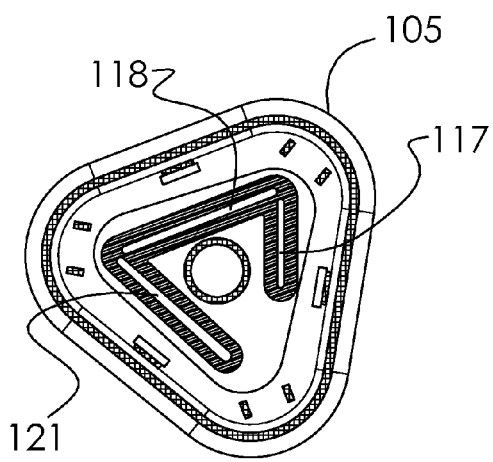
Figure 6B:
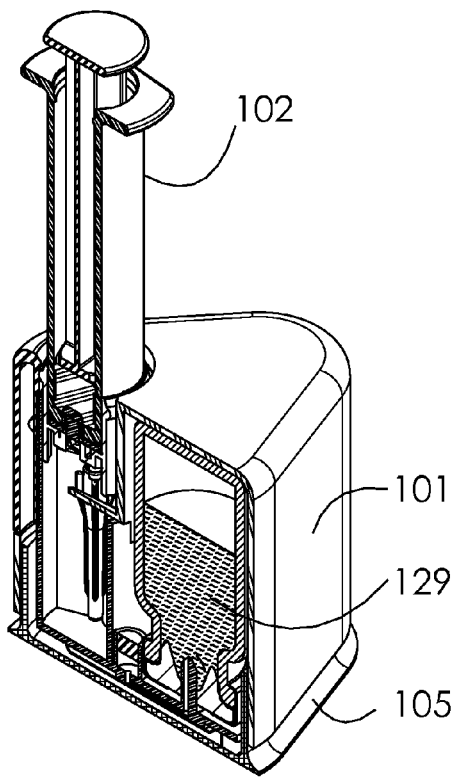

FIG. 6C illustrates a sectioned top view of lower housing element flange 105, which when overlaid with base cover (not shown, see, e.g., FIG. 11B, callout 333), creates the isolated fluid conduits 117, 118, and 121 from formed channels.

Figure 6D:
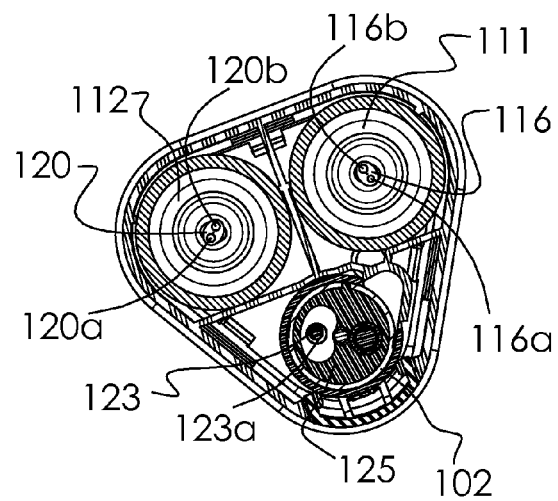

FIG. 6D shows the sectional view of the upper housing revealing lumens 116a, 116b of spike 116, lumens 120a, 120b of spike 120, and lumen 123a of spike 123.

Figures 7A, 7B:
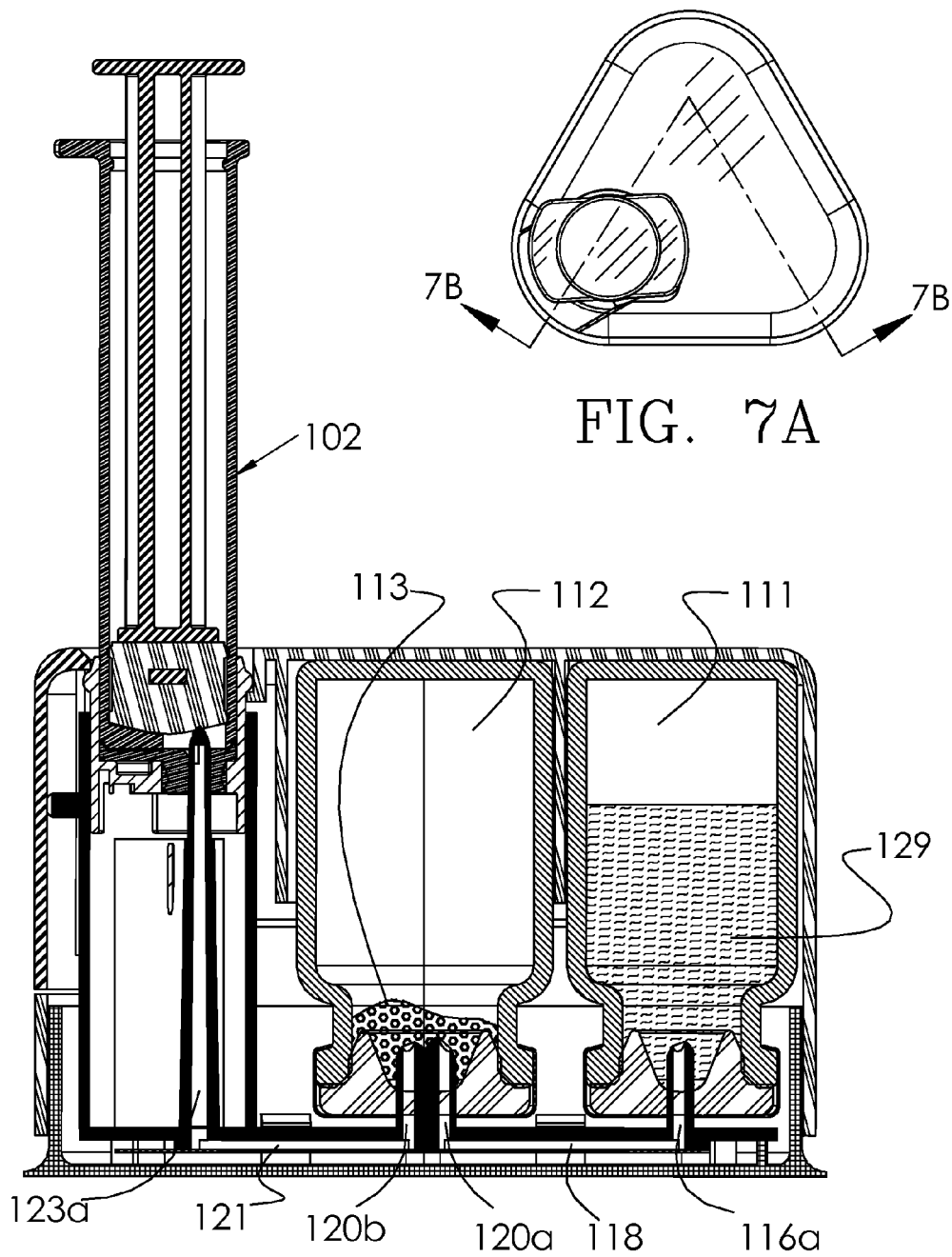
FIGS. 7A-7B are section plane and corresponding cross-sectional views of the transfer and delivery device of FIG. 1 in an immediate activated state, as disclosed and described herein.

FIGS. 7A-7B are section plane and corresponding cross-sectional views of the first embodiment device in its activated state, in a theoretical instance just before any fluid transfer has taken place. Container accessing members 116, 120, and 123 (FIG. 6D) have sealably pierced their respective media containers 111, 112, and 102, providing fluid communication between vent, vent conduit (FIG. 6D), first container 111 containing fluid 129, first fluid conduit 118, intermediate container 112 containing drug media 113 under vacuum, second fluid conduit 121, and syringe 102.

Figure 8A:
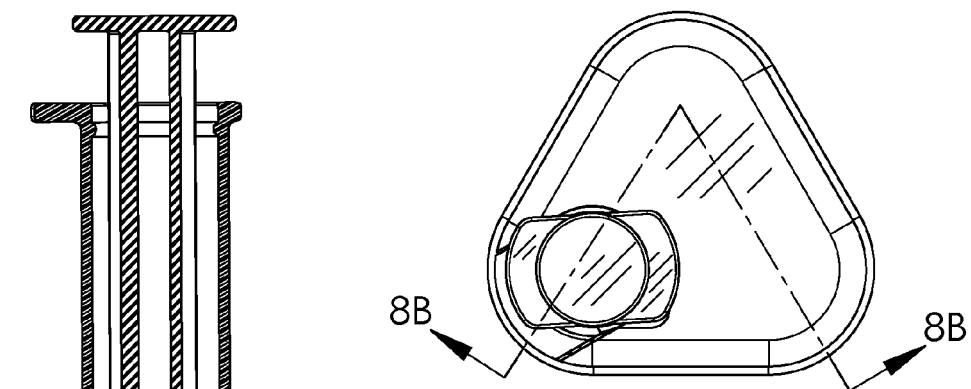
FIGS. 8A-8B are section plane and corresponding cross-sectional views of the transfer and delivery device of FIG. 1 in its activated state a moment after the state as depicted in FIG. 7B.
Figure 8B:
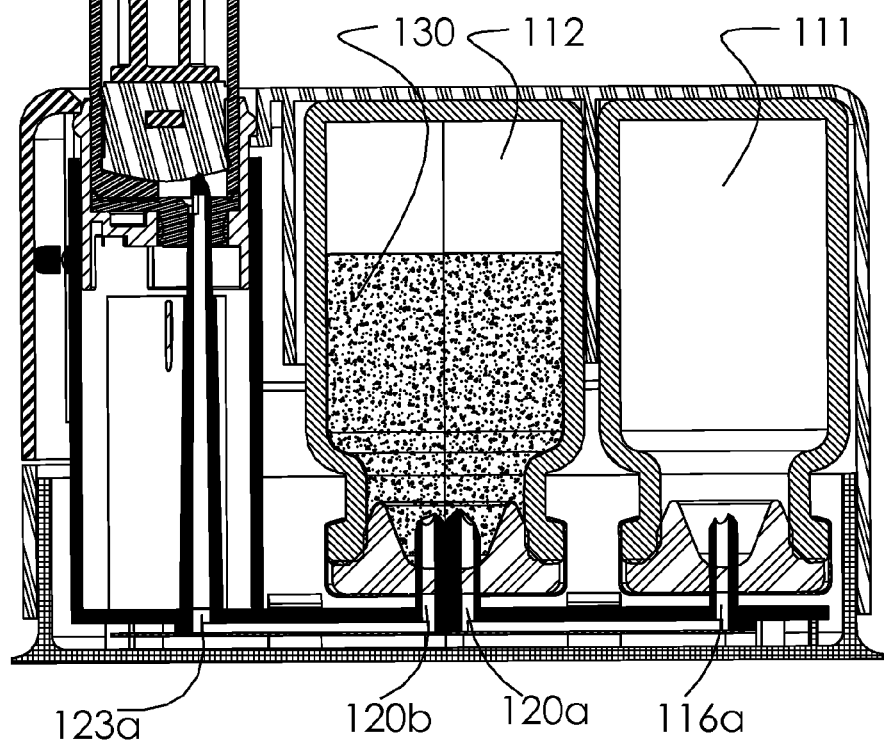

FIGS. 8A-8B are section plane and corresponding cross-sectional views of the first embodiment device in its activated state a moment after the state depicted in FIG. 7B, where the pre-existing vacuum of second container 112 has drawn in the fluid from first container 111 and has allowed the fluid to mix with the drug media in second container 112, providing drug mixture 130, which can be a solution, suspension, dispersion oil-in-water or water-in-oil, gel, and the like. As shown, each of the elongate container accessing members (i.e., 116, 120) and the delivery device accessing member 123 project in the same direction relative to the base of the lower housing.

FIGS. 9A-9B are section plane and corresponding cross-sectional views of the first embodiment device in its activated state, where drug mixture 130 has been drawn from the second container 112 into syringe 102 interior volume 125 by drawing back syringe plunger rod 108. The drug mixture has passed through fluid lumen 123a of accessing member 123 which is sealably penetrating syringe septum 109 and into the syringe interior volume 125 via conduit opening 124a. Displaced volume of fluid container 111 is accommodated via vent 117a (see FIG. 3B).

FIGS. 10A-10B are perspective views of a second embodiment fluid transfer and delivery device 200 having base flange 205 supporting lower housing 204, which slideably receives upper housing 201, in which the first media container 111 and second media container 212 can be added, removed or exchanged by means of an access 227 with hinge means 220 and latch means 225. Syringe 102 with plunger rod 108 is provided as above.

FIGS. 11A-11B are a perspective view and exploded view of a third embodiment of device 300 having upper housing 301 slideably received by lower housing 304, with alignment means 301a and 304a, respectively. Syringe release catch 303b is adapted to top 301b of upper housing 301 to serve as reversible locking means for the syringe 302b. Optional gripping features 328a and 328b can be added to the top and sides of the upper housing. Syringe 302b has a passive needle safety feature 350. FIG. 11B depicts the exploded view with the relationship between the syringe, containers and fluid conduit system of device 300. Additional incidental details of this design depicted in FIGS. 11A & 11B, including detents 331a, 331b in top 301b of upper housing 301 that interacts with the syringe release catch to create an "open" and "closed" position, respectively; locking feature 332 on the lower housing 304 that interacts with a corresponding catch feature on the upper housing to hold the components together in the as-assembled and accessed positions. Also shown are the three spikes 316b, 320b, 323b that pierce the septums 111a, 112a of media containers 111, 112, respectively and syringe septum of syringe 302b respectively; end of the vent conduit 317b, and the flat sheet or film component 333, that when overlaid with the lower housing 304 with integrated channels, forms the flow conduits 317, 318, and 321 (not shown) connecting the corresponding lumens in spikes 316b, 320b, 323b and vent conduit 317b.

Figure 12A:
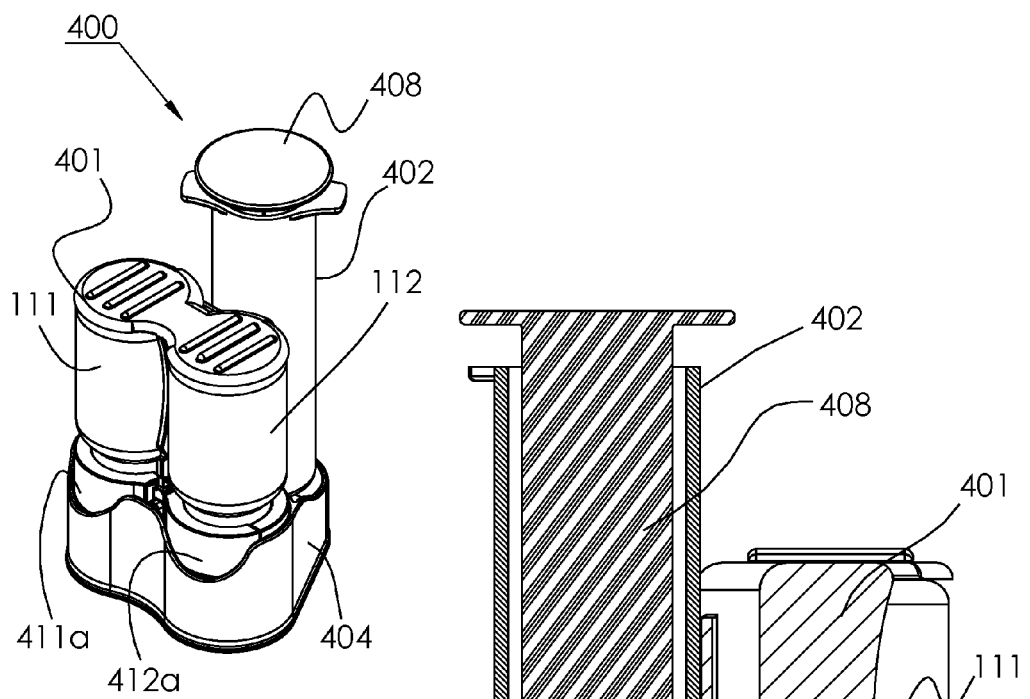
FIGS. 12A-12C are an orthogonal, top and section view, respectively, of a fourth embodiment of the device, as disclosed and described herein.
Figure 12B:
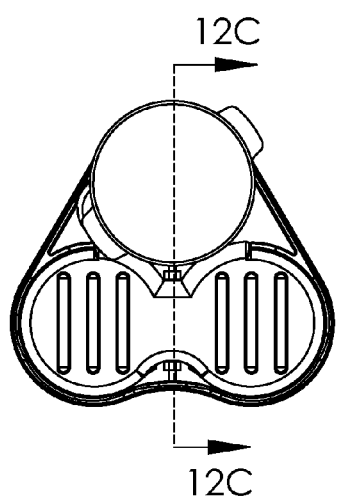
Figure 12C:
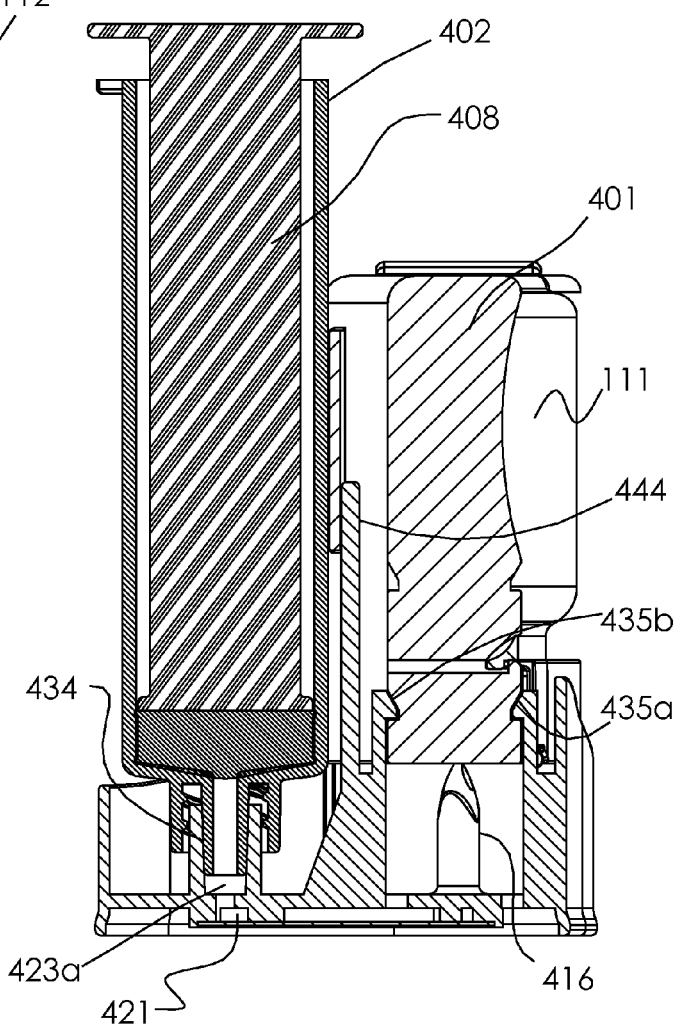

FIGS. 12A-12C are an orthogonal, top and section view respectively of fourth embodiment device 400 having upper housing 401 slidably engaging lower housing 404, and fluid conduit 421 with syringe securing member 434 with lumen 423a in the lower housing 404 for connecting syringe 402 with plunger 408. Device 400 lacks a piercing syringe accessing member and is adapted with a syringe accessing member suitable for securing a conventional syringe to the lower housing, specifically, a syringe securing member. Syringe securing member may include, for example, a luer-lok adapters, luer fittings, and other threaded or tolerance fittings. Guide features/locking means 444, 435a, and 435b, together with container locking features 411a, 412a secures upper and lower housings and containers in the as-assembled and accessed positions.

FIGS. 13A-13C are perspective view and exploded view of the fourth embodiment device 400. In FIG. 13A the upper housing includes access 427 to enable loading of the media containers 111, 112 and gripping features 428a have been added to the top of the upper housing. The access may be comprised of two or more separate components, hinged at one or more locations, or may be included in the upper housing with a living hinge feature. In the exploded view FIG. 13B the relationship between these components can be seen. Guide feature 444 in the lower housing 404 supports the upper housing 401b, locking features 435a, 435b in the lower housing interacts with corresponding catch features 436 on the upper housing to hold the components together in the as-assembled and accessed positions. The upper housing also includes undercut securing features 437a, 437b for receiving container closures 111a, 112a. Also shown are two spikes 416a, 420b that pierce media containers 111, 112 pierceable septums. Syringe 402 is shown connected to a luer connection 438 adjacent to vent 417b. As shown, each of the elongate container accessing members (i.e., 416a, 420b) and the delivery device accessing member (i.e., luer connection 438) project in the same direction relative to the base of the lower housing. Flat sheet or film component 433 that when overlaid with the lower housing 404 closes the molded channels 417c, 418c, and 421c (referring to perspective view of lower housing 404, FIG. 13C) to form the fluid conduits 417, 418, and 421 (not shown) for fluid communication with lumens of spikes 416a, 420b and luer connection 438 and vent 417b. Fluid conduits 417, 418 and 421 are physically isolated from each other. The dual lumens of the spikes connect these isolated fluid conduits together, to provide at least a portion of a fluidic conduit system. In one aspect, a fluidic conduit system is formed upon assembly of the flat sheet or film component 433 (or a base) with the lower housing 404 and provides fluid communication between at least two of spikes and/or compartments of the device.

FIGS. 14A-14B are perspective views of fluid transfer and delivery device 400 in which the first media container 111 and second media container 112 can be added, removed or exchanged by means of an access 427 with hinge means for providing opening for receiving the container closure portions 111a, 112a of containers 111, 112 respectively.

In use, to transfer fluid between the first and intermediate containers in device 400, mix or dissolve the drug, and transfer the mixture to the syringe for administration or dispensing, a external force, typically by the hand of a user, is employed to telescopically collapse the upper housing into the lower housing of the device and subsequently allow the media container accessing spikes to pierce their respective media containers. Vacuum preconditioned in the second container as is often found in lyophilized drug vials, for instance creates a pressure differential when sealably accessed thereby causing the fluid of the first container to fluidically navigate the first fluid conduit and be deposited into the intermediate media container. At this time, filtered air is likewise drawn into the first container for pressure equalization via the vent conduit. The contents of the intermediate container may then be agitated in a manner appropriate to the mixture. Drawing back on the syringe plunger rod creates a pressure differential between the intermediate container and the interior of the syringe causing the mixed drug to fluidically navigate the second fluid conduit and be deposited into the interior volume of the syringe. At this time, filtered air is likewise drawn into the system by way of the vent conduit and subsequent conduits for pressure equalization.

FIGS. 15A-15B are a perspective view and exploded view, respectively, of a fifth embodiment device 500. In FIG. 15A the upper housing 501 is received by lower housing 504, which includes container access cutout 527b to enable loading of only one container (e.g., container 112) after manufacturing assembly. Gripping features 528a have been added to the top of the upper housing. In the exploded view FIG. 15B the relationship between these components can be seen. Guide feature 534 in the lower housing 504 supports the upper housing. Locking features 535a in the lower housing interact with corresponding catch features 536 on the upper housing to hold the components & housing sections together in the as-assembled and accessed positions. Also shown are two spikes 516b, 520b that pierce media containers 111, 112 pierceable septum's respectively. Syringe 502 is received by connection not shown in lower housing 504. Flat sheet or film component 533 when overlaid with the lower housing 504 closes the molded channels to create the fluid conduits 517, 518, and 521 not shown creating the corresponding fluid conduits connecting spikes 516b, 520b, vent 517b and connection for syringe not shown.

In use, the user must first load the intermediate media container (which may contain a drug) into the device by inserting it into the container access 527a, 527b. Then to transfer fluid between the first and intermediate containers in device 500, mix or dissolve the drug, and transfer the mixture to the syringe for administration or dispensing, an external force, typically by the hand of a user, is employed to urge the upper housing into the lower housing of the device and subsequently allow the media container accessing spikes to pierce their respective media containers. Vacuum preconditioned in the second container as is often found in lyophilized drug vials, for instance creates a pressure differential when sealably accessed thereby causing the fluid of the first container to fluidically navigate the first fluid conduit and be deposited into the intermediate media container. At this time, filtered air is likewise drawn into the first container for pressure equalization via the vent conduit. The contents of the intermediate container may then be agitated in a manner appropriate to the mixture. Drawing back on the syringe plunger rod creates a pressure differential between the intermediate container and the interior of the syringe causing the mixed drug to fluidically navigate the second fluid conduit and be deposited into the interior volume of the syringe. At this time, filtered air is likewise drawn into the system by way of the vent conduit and subsequent conduits for pressure equalization.

Packaging

In another aspect, the above device embodiments are packaged in a way such that a container comprising a sterilizing-sensitive media can be packaged separately with a pre-sterilized device. In this way, the sterilizing-sensitive media to be dissolved, reconstituted or otherwise combined with the contents of a second container, for example a diluent or solvent, can be packaged together with the device. In another aspect, the device and at least one container can be assembled in a kit and packaged under aseptic conditions, for example, to provide a combination of containers (e.g., media and diluent).

Figure 16A:
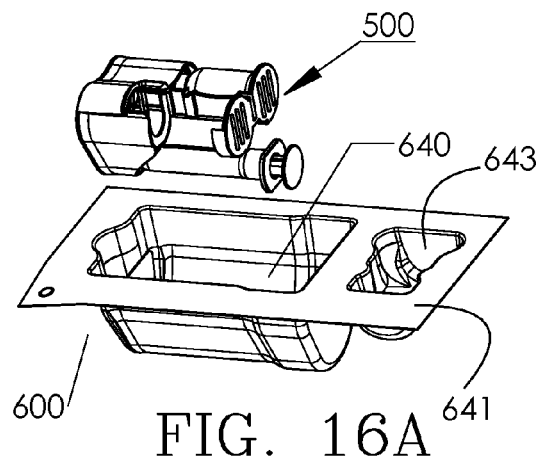
FIGS. 16A-16E are perspective views of a packaging system for the transfer and delivery device as disclosed and described herein.
Figure 16B:
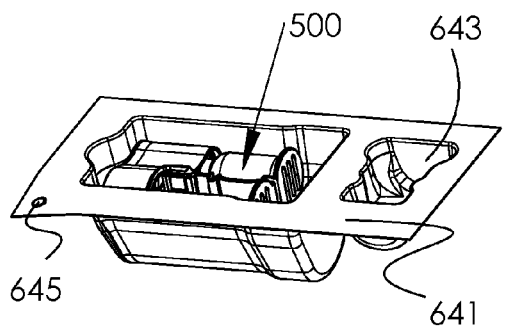
Figure 16C:
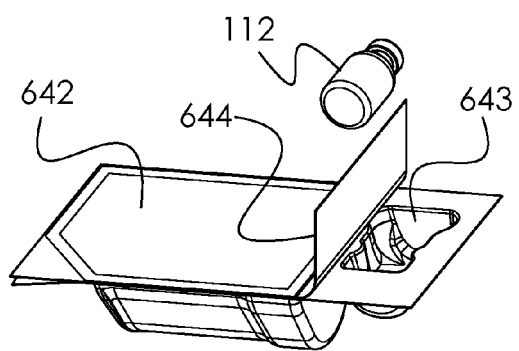
Figure 16D:
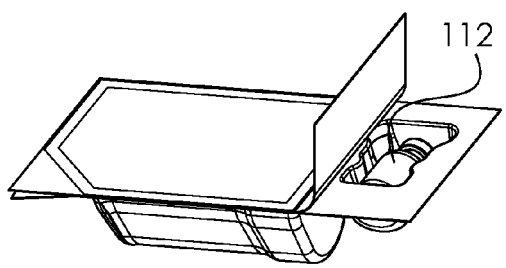
Figure 16E:
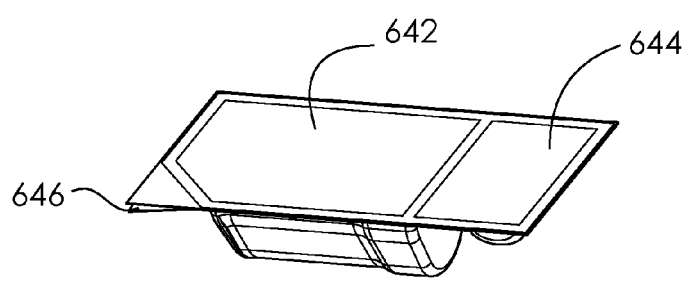
Figure 17A:
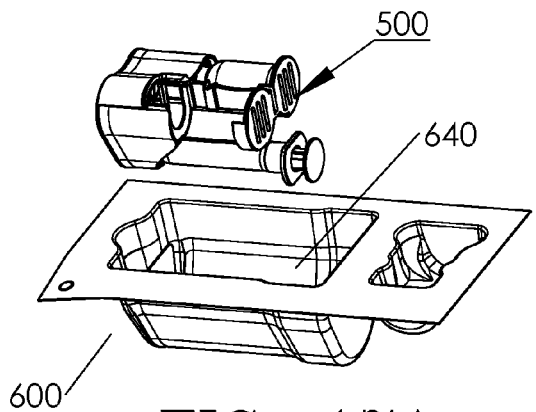
FIGS. 17A-17E are perspective views of a packaging system for the transfer and delivery device as disclosed and described herein.
Figure 17B:
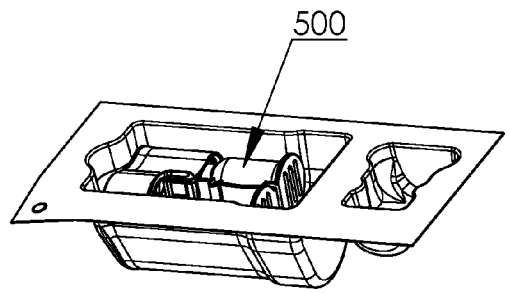
Figure 17C:
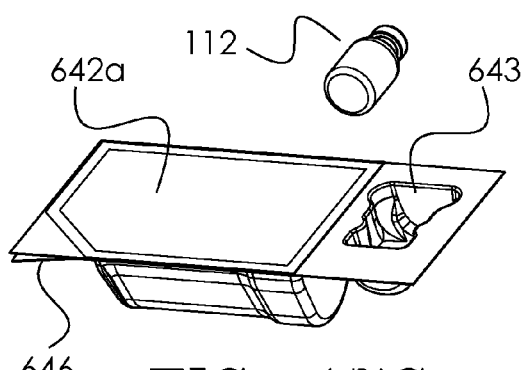
Figure 17D:
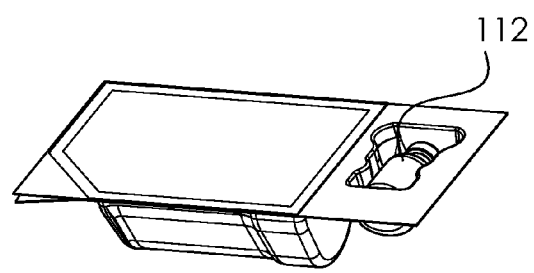
Figure 17E:
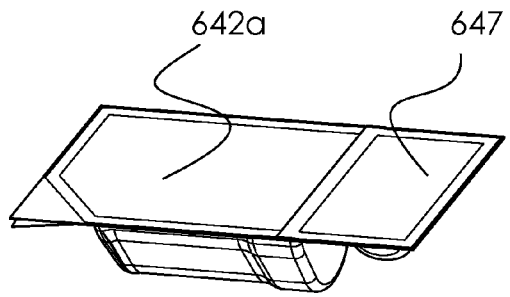

Thus, referring to FIG. 16A, partitioned packaging element 600 comprising first receptacle 640 adapted for receiving the device, e.g., 500 with optional liquid containing first container, is shown. FIG. 16B depicts device 500 received by package with raised feature 645 on face 641. FIG. 16C depicts lid 642 sealably configured to face 641 with un-sealed portion 644 aligned with second receptacle 643 adapted for receiving sterilizing-sensitive media of second container 112. Lid can be of continuous construction or can be provided in separate components adapted for the corresponding receptacles. Prior to receipt of sterilizing-sensitive media of container 112, the packaging element 600 with device and optional liquid container can be sterilized, for example, by high energy radiation, hydrogen peroxide, or ethylene oxide. Subsequent to the sterilization of packaging element 600 with device 500 and optional liquid container, the sterilizing-sensitive media of second container 112 can be received by second receptacle 643, optionally under aseptic conditions. Raised feature 645 allows for assistance with opening. FIGS. 17A-17E depicts packaging element 600 with first lid 642a configured to seal only first receptacle 640. Subsequent to the sterilization of packaging element 600 with device 500 and optional liquid container, the sterilizing-sensitive media of second container 112 can be received by second receptacle 643, and sealed with second lid 647. Lids 642 and/or 647 can be of any suitable material, for example peelable film or Tyvek®, for ease of release from face of packaging member or can be of a paper construct for pushing the device and/or container through.

FIGS. 18A-18D depicts the releasing of the sheet from the tray via separated section 646 of packaging element 600 (FIG. 16A) caused by raised feature, and introduction of the sterilizing-sensitive media of container 112 into device 500 via container access cutout 527.

Figure 18A:
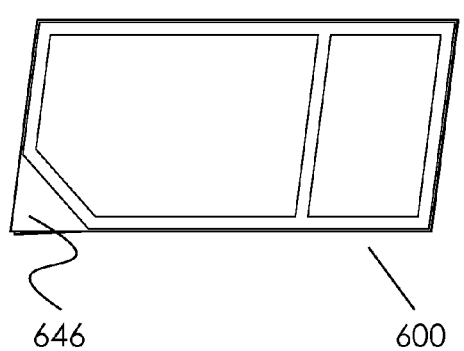
FIGS. 18A-18D are perspective views of a packaging system for the transfer and delivery device as disclosed and described herein.
Figure 18B:
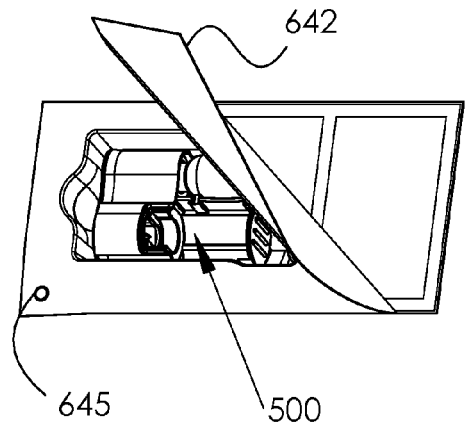
Figure 18C:
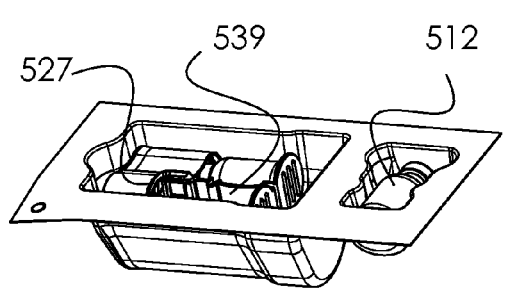
Figure 18D:
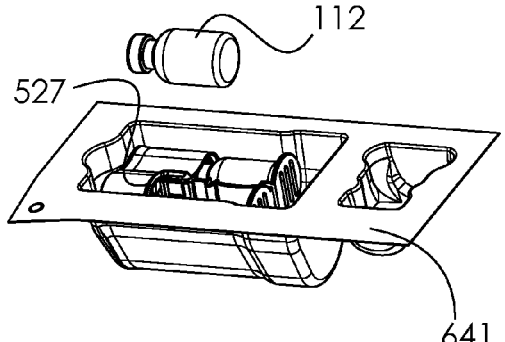
Figure 18E:
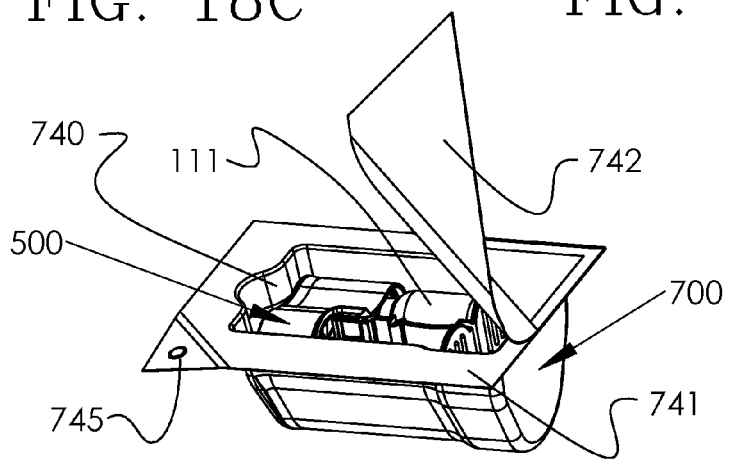
FIG. 18E is a perspective view of a packaging system for the transfer and delivery device and first container without second container.

FIG. 18E depicts an embodiment of kit 700 comprising any of the previously described transfer devices (e.g., 500 as shown) and first container 111, which can contain a suitable diluent, solvent, or other transferable substance. Package 741 provides a suitable receptacle for the transfer device and first container and comprises releasing lid 742 and releasing aid 745. Thus, the kit provides for packaging the transfer device with only the diluent for a substance that is to be provided separately at some later point in time. Kit 700 also provides for sterilization methods otherwise unacceptable to certain medicaments, for example, biologics. Upon use, the end-user would release the transfer device and associated (or pre-assembled, un-accessed) first container assembly from the receptacle and introduce the medicament (e.g., for dilution or for reconstitution) into the upper housing 501, which includes container access cutout 527 to enable loading of only one container (e.g., 112, which can comprise medicament (not shown). Activation of the device as described above for device 500 provides for the transfer and mixing of the components of containers, e.g., 111 and 112.

Manufacturing

All of the components of the proposed embodiments may be injection molded with the exception of the syringe needle and drug vials. Alternate manufacturing methods for the elastomeric components may include compression or transfer molding. An alternate manufacturing method for the packaging element may include thermoforming. Design intent may be such that components are molded with simple open/close tooling where possible to reduce tooling cost and cycle times. The fluid conduits as seen, for example in FIG. 5C, at callouts 117, 118, 121 may be formed by injection molding, where the conduits are channels formed in one plane in an "open-topped" configuration (as shown in FIG. 13C at similar callouts 417c, 418c, and 421c), and which are subsequently closed to create separate conduits by adhering a flat sheet or film of suitable material across the open-topped surface. The flat sheet or film may be laser welded, ultrasonically welded, heat sealed, solvent bonded, and the like. The flat sheet or film may be die cut rather than injection molded as appropriate.

Where feature definition may not be able to be achieved by single tool molding; ultrasonic welding, adhesives or mechanical retention may be employed to join components. Furthermore, where dissimilar materials may be advantageous, a 2-shot molding technique may be utilized, such as creating a non-slip surface to the bottom flange of the lower housing.

Reduced Procedural Steps

The device described herein may reduce the number of steps required to prepare a mixture. The combination of accessing multiple vials in a single stroke as well as having negatively pressurized media containers to compel the transfer of fluids rather than manual human interaction may prove to significantly reduce the steps required when compared to contemporary transfer devices of this kind. Additionally, by sterilizing the packaged device as described herein, the use of an antiseptic solution can be avoided when preparing the medicament containers for access.

Multiple Media Container Access Via External Force

The device described herein may allow for accessing multiple media containers when a single force is applied. The force required for this action may be mitigated by the increased ergonometric arrangement of the device. The inherent stability of multiple points of contact and substantial guiding surfaces make the device significantly easier to operate.

Reduced Manufacturing Complexity

The device described herein uses standard drug vials as opposed to prefilled syringes. Often prefilled syringe systems are assumed to reduce the number of steps and/or simplify the preparation and administration process. The device described here eliminates the need to attach the prefilled syringe plunger and the need to inject the diluent into the drug vial. This reduces steps over comparable prefilled syringe systems and is more compact, allowing for saved space in clinical and home environments and its inclusion in automated pharmacy systems. The device eliminates the complexity of validation and filling when compared to prefills, allows for full flexibility of varying the volume of drug vials, and utilizes existing processes and stability data readily available by filling standard drug vials. This results in lower costs as well in most cases. Also, by eliminating pre-filled syringes, the syringe herein may be more readily customized for the specific application, employing features like passive needle safety, or other fittings such as spray nozzles, varying needle types, valved male luers, or capped slip or locking style luers. The syringe volume can be readily varied, and since the drug is contained for short durations within, there are fewer limitations with regards to gas or moisture barrier properties, extractables, leachables, or other drug compatibilities.

We claim:

1. A transfer device comprising:
a housing comprising:
   a base; and
   a lower housing assembled to the base, the lower housing slidably receiving an upper housing; wherein the lower housing defines three compartments, two of the three compartments configured for receiving a container having a pierceable portion, and one of the compartments configured to engage a delivery device with a dispensing member, the delivery device having a pierceable fluid by-pass element adjacent the dispensing member;
a fluidic conduit system formed upon assembly of the base with the lower housing for providing fluid communication between at least two of the three compartments, wherein the fluidic conduit system comprises:
   (i) a vent;
   (ii) a first container accessing member having a longitudinal axis distally projecting essentially vertical from the base, and having corresponding therewith a first fluid lumen and a second fluid lumen essentially parallel with the longitudinal axis, the first fluid lumen of the first elongate container accessing member in fluid communication with the vent;
   (iii) a second container accessing member having a longitudinal axis distally projecting essentially vertical from the base, and having corresponding therewith a first fluid lumen and a second fluid lumen essentially parallel with the longitudinal axis, the first fluid lumen of the second elongate container accessing member in fluid communication with the second fluid lumen of the first elongate container accessing member; and
   (iv) a delivery device accessing member having a longitudinal axis distally projecting essentially vertical from the base, and having corresponding therewith a first fluid lumen essentially parallel with the longitudinal axis, the first fluid lumen of the third elongate delivery device accessing member in fluid communication with the second fluid lumen of the second elongate container accessing member.

2. The device of claim 1, wherein the base comprises:
   (i) a first flow channel fluidically communicating the first fluid lumen of the first container accessing member with the vent;
   (ii) a second flow channel fluidically communicating the first fluid lumen of the second container accessing member with the second fluid lumen of the first container accessing member, and
   (iii) a third flow channel fluidically communicating the first fluid lumen of the delivery device accessing member with the second fluid lumen of the second container accessing member;
   the first, second, and third flow channels (i)-(iii) being physically isolated from each other and forming at least a portion of the fluidic conduit system upon assembly of the base and the lower housing.

3. The device of claim 1, wherein each of the longitudinal axes of the first container accessing member, the second container accessing member, and the delivery device accessing member distally project in the same direction relative to the base.

4. The device of claim 1, with the proviso that the fluidic conduit system is devoid of a flow controlling device.

5. The device of claim 1, further comprising a first container comprising a liquid, the container operably positioned with the first container accessing member.

6. The device of claim 1, further comprising a second container comprising a medicament, the second container operably positioned with the second container accessing member.

7. The device of claim 1, further comprising a delivery device having the pierceable fluid by-pass element operably positioned with the delivery device accessing member.

8. A transfer device comprising:
a housing comprising:
a base; and
a lower housing assembled to the base, the lower housing slidably receiving a portion of an upper housing; wherein the lower housing defines multiple compartments, at least two of the multiple compartments associated with the portion of the upper housing and configured for receiving at least two containers, each having a pierceable portion associated therewith, and one of the multiple compartments configured to receive a delivery device; and
a fluidic conduit system integral with the base providing fluid communication between at least two of the multiple compartments,
wherein the fluidic conduit system comprises:
(i) a vent;
(ii) a first container accessing member having a longitudinal axis distally projecting essentially vertical from the base, and having corresponding therewith a first fluid lumen and a second fluid lumen essentially parallel with the longitudinal axis, the first fluid lumen of the first elongate container accessing member in fluid communication with the vent;
(iii) a second container accessing member having a longitudinal axis distally projecting essentially vertical from the base, and having corresponding therewith a first fluid lumen and a second fluid lumen essentially parallel with the longitudinal axis, the first fluid lumen of the second elongate container accessing member in fluid communication with the second fluid lumen of the first elongate container accessing member; and
(iv) a delivery device accessing member having a longitudinal axis distally projecting essentially vertical from the base, and having corresponding therewith a first fluid lumen essentially parallel with the longitudinal axis, the first fluid lumen of the delivery device accessing member in fluid communication with the second fluid lumen of the second elongate container accessing member
wherein the base comprises:
(i) a first flow channel fluidically communicating the first fluid lumen of the first container accessing member with the vent;
(ii) a second flow channel fluidically communicating the first fluid lumen of the second container accessing member with the second fluid lumen of the first container accessing member, and
(iii) a third flow channel fluidically communicating the first fluid lumen of the delivery device accessing member with the second fluid lumen of the second container accessing member;
the first, second, and third flow channels (i)-(iii) being physically isolated from each other and forming at least a portion of the fluidic conduit system upon assembly of the base and the lower housing.

9. The device of claim 8, with the proviso that the fluidic conduit system is devoid of a flow controlling device.

10. The device of claim 8, wherein each of the longitudinal axes of the first elongate container accessing member, the second elongate container accessing member, and the delivery device accessing member distally project in the same direction relative to the base.

11. The device of claim 8, further comprising a first container comprising a liquid, the first container operably positioned with first elongate container accessing member.

12. The device of claim 8, further comprising a second container comprising a medicament, the second container operably positioned with second elongate container accessing member.

13. The device of claim 8, further comprising a syringe operably positioned with the delivery device accessing member.

14. A method of mixing and transferring, the method comprising:
providing a device, the device comprising: a housing comprising:
a base; and
a lower housing assembled to the base, the lower housing slidably receiving an upper housing; wherein the lower housing defines at least two compartments, two of the three compartments configured for receiving a container having a pierceable portion, and one of the compartments configured to engage a delivery device; and
a fluidic conduit system integral with the base providing fluid communication between the at least two compartments;
applying an external force to slidably receive the upper housing into the lower housing; transferring the contents of a first container to a second container via the fluidic conduit system; and
mixing at least a portion of the contents of the first container with at least a portion of the contents of the second container
wherein the fluidic conduit system comprises:
(i) a vent;
(ii) a first container accessing member having a longitudinal axis distally projecting essentially vertical from the base, and having corresponding therewith a first fluid lumen and a second fluid lumen essentially parallel with the longitudinal axis, the first fluid lumen of the first elongate container accessing member in fluid communication with the vent;
(iii) a second container accessing member having a longitudinal axis distally projecting essentially vertical from the base, and having corresponding therewith a first fluid lumen and a second fluid lumen essentially parallel with the longitudinal axis, the first fluid lumen of the second elongate container accessing member in fluid communication with the second fluid lumen of the first elongate container accessing member; and
(iv) a delivery device accessing member having a longitudinal axis distally projecting essentially vertical from the base, and having corresponding therewith a first fluid lumen essentially parallel with the longitudinal axis, the first fluid lumen of the delivery device accessing member in fluid communication with the second fluid lumen of the second elongate container accessing member
wherein the base comprises:
(i) a first flow channel fluidically communicating the first fluid lumen of the first container accessing member with the vent;

(ii) a second flow channel fluidically communicating the first fluid lumen of the second container accessing member with the second fluid lumen of the first container accessing member, and (iii) a third flow channel fluidically communicating the first fluid lumen of the delivery device accessing member with the second fluid lumen of the second container accessing member;

the first, second, and third flow channels (i)-(iii) being physically isolated from each other and forming at least a portion of the fluidic conduit system upon assembly of the base and the lower housing.

15. The method of claim 14, with the proviso that the fluidic conduit system is devoid of a flow controlling device.

16. The method of claim 14, further comprising transferring at least a portion of the contents from the second container into the delivery device, the delivery device comprising a syringe.

17. A kit comprising
a transfer device as defined in claim 1;
a first container adapted for receipt by the transfer device, the first container comprising a fluid; and
optionally, a packaging member.

18. The kit of claim 17, wherein the packaging member further comprises a first receptacle configured to receive the transfer device and the first container; and a lid sealable across the first receptacle.

19. The kit of claim 17, further comprising a second container and wherein the packaging member is configured to separately receive second container in a second receptacle.

20. The kit of claim 17, wherein the transfer device and a first container and/or a second container are operably assembled for use.

21. A kit comprising
a transfer device as defined in claim 14;
a first container adapted for receipt by the transfer device, the first container comprising a fluid; and
optionally, a packaging member.

22. The kit of claim 21, wherein the packaging member further comprises a first receptacle configured to receive the transfer device and the first container; and a lid sealable across the first receptacle.

23. The kit of claim 21, further comprising a second container and wherein the packaging member is configured to separately receive second container in a second receptacle.

24. The kit of claim 21, wherein the transfer device and a first container and/or a second container are operably assembled for use.

25. A method of packaging a transfer device for sterilization, the method comprising:
providing a packaging member, the packaging member comprising: a first receptacle configured to receive a transfer device optionally with a first container; and
optionally, a second receptacle configured to separately receive a second container comprising a material sensitive to a sterilization condition;
receiving a transfer device as defined in claim 1 into the first receptacle.

26. The method of claim 25, further comprising receiving the second container into the second receptacle.

27. The method of claim 26, further comprising receiving the second container into the second receptacle after completion of a sterilization condition.

28. The method of claim 26, further comprising providing a lid over at least the second receptacle.

29. The method of claim 27, wherein the lid is partitioned across the first receptacle and the second receptacle.

30. The method of claim 25, wherein the sterilization condition is thermal, high energy radiation, or chemical.

31. The method of claim 26, wherein the second container comprises a biologic drug.

32. A method of sterilization, the method comprising:
packaging a transfer device as defined in claim 1, optionally with a first container in a packaging member, the packaging member comprising:
a first receptacle configured to separately receive the transfer device and the optional first container; and
a second receptacle configured to separately receive a second container;
sealing the first receptacle;
sterilizing the transfer device and the optional first container with a sterilization condition;
introducing a second container to the second receptacle, the second container comprising a material sensitive to the first sterilization condition; and
optionally sealing the second receptacle.

33. The method of claim 32, wherein the second container comprises a biologic drug.

34. The method of claim 32, wherein the sterilization condition is thermal, high energy radiation, or chemical.

35. The method of claim 32, wherein the first container and/or the second container is introduced to the respective first receptacle and second receptacle in an aseptic environment.

* * * * *